(12) United States Patent
Benuri-Silbiger

(10) Patent No.: US 10,695,270 B2
(45) Date of Patent: Jun. 30, 2020

(54) DEVICES AND METHODS FOR PERCUTANEOUS ENDOSCOPIC GASTROSTOMY AND OTHER OSTOMY PROCEDURES

(71) Applicant: Hadasit Medical Research Services and Development Ltd., Jerusalem (IL)

(72) Inventor: Ishay Benuri-Silbiger, Jerusalem (IL)

(73) Assignee: Hadasit Medical Research Services and Development Ltd., Jerusalem (IL)

(*) Notice: Subject to any disclaimer, the term of this patent is extended or adjusted under 35 U.S.C. 154(b) by 0 days.

(21) Appl. No.: 14/900,160

(22) PCT Filed: Jun. 19, 2014

(86) PCT No.: PCT/IL2014/050559
§ 371 (c)(1),
(2) Date: Dec. 20, 2015

(87) PCT Pub. No.: WO2014/203259
PCT Pub. Date: Dec. 24, 2014

(65) Prior Publication Data
US 2016/0143816 A1 May 26, 2016

Related U.S. Application Data

(60) Provisional application No. 61/837,184, filed on Jun. 20, 2013.

(51) Int. Cl.
*A61J 15/00* (2006.01)
*A61M 25/02* (2006.01)
*A61M 39/08* (2006.01)

(52) U.S. Cl.
CPC ......... *A61J 15/0038* (2013.01); *A61J 15/003* (2013.01); *A61M 2025/0233* (2013.01); *A61M 2039/085* (2013.01)

(58) Field of Classification Search
CPC ............... A61J 15/0015; A61J 15/0019; A61J 15/0023; A61J 15/003; A61J 15/0034;
(Continued)

(56) References Cited

U.S. PATENT DOCUMENTS 3,834,394 A * 9/1974 Hunter ............. A61B 17/12031
604/907
4,471,779 A * 9/1984 Antoshkiw ...... A61B 17/12109
604/907
(Continued)

FOREIGN PATENT DOCUMENTS

| CN | 1780599 | 5/2006 |
|---|---|---|
| CN | 101905058 | 12/2010 |

(Continued)

OTHER PUBLICATIONS

International Search Report and the Written Opinion dated Apr. 25, 2016 From the International Searching Authority Re. Application No. PCT/IL2015/051252.
(Continued)

*Primary Examiner* — Bhisma Mehta
*Assistant Examiner* — Laura C Schell

(57) ABSTRACT

Ostomy tubes, particularly gastrostomy tubes, with improved retention means are provided. More specifically, retention structures, such as bolsters, for gastrostomy tubes are provided, configured to removably assemble to one end of a gastrostomy tube to facilitate replacement and removal of the tube. The retention structures provided herein may comprise one or more removably assembled retention elements. Further provided are gastrostomy tubes comprising such retention structures, and methods for percutaneous endoscopic gastrostomy utilizing same.

24 Claims, 13 Drawing Sheets

(58) Field of Classification Search
CPC ............. A61J 15/0042; A61J 15/0026; A61J 15/0038; A61J 15/0046; A61J 15/0049; A61J 15/0057; A61J 15/0065; A61J 15/0069; A61J 15/0073; A61M 2039/085; A61M 2025/0233; A61M 25/0071; A61M 25/10; A61M 25/0017; A61M 3/0291

See application file for complete search history.

(56) References Cited

U.S. PATENT DOCUMENTS

| | | | | |
|---|---|---|---|---|
| 4,710,169 | A | * | 12/1987 | Christopher .......... A61M 25/04 128/DIG. 25 |
| 4,944,732 | A | | 7/1990 | Russo |
| 5,073,166 | A | * | 12/1991 | Parks ................ A61J 15/0015 604/105 |
| 5,356,382 | A | | 10/1994 | Picha et al. |
| 5,356,391 | A | | 10/1994 | Stewart |
| 5,391,159 | A | | 2/1995 | Hirsch et al. |
| 5,556,385 | A | | 9/1996 | Andersen |
| 5,797,939 | A | * | 8/1998 | Yoon ..................... A61B 17/122 606/167 |
| 6,039,714 | A | | 3/2000 | Cracauer et al. |
| 6,045,536 | A | | 4/2000 | Meier et al. |
| 6,186,985 | B1 | | 2/2001 | Snow |
| 6,485,476 | B1 | * | 11/2002 | von Dyck ............... A61F 5/441 600/29 |
| 6,666,853 | B2 | | 12/2003 | Chu et al. |
| 6,976,980 | B2 | | 12/2005 | Brenner et al. |
| 7,582,072 | B2 | | 9/2009 | McMichael |
| 7,637,915 | B2 | | 12/2009 | Parmer et al. |
| 8,475,430 | B2 | | 7/2013 | Adams et al. |
| 8,480,652 | B2 | | 7/2013 | Renaux et al. |
| 8,834,370 | B2 | | 9/2014 | Evert et al. |
| 2002/0198440 | A1 | * | 12/2002 | Snow ................... A61J 15/0023 600/116 |
| 2003/0163119 | A1 | | 8/2003 | Chu et al. |
| 2003/0225376 | A1 | | 12/2003 | Fournie et al. |
| 2004/0059293 | A1 | * | 3/2004 | Chu .................... A61J 15/0015 604/107 |
| 2004/0092973 | A1 | * | 5/2004 | Chanduszko ...... A61B 17/3478 606/151 |
| 2005/0033240 | A1 | | 2/2005 | Oishi et al. |
| 2005/0059929 | A1 | * | 3/2005 | Bolmsjo ........... A61M 25/0017 604/96.01 |
| 2006/0052752 | A1 | | 3/2006 | McMichael |
| 2006/0116658 | A1 | | 6/2006 | McMichael et al. |
| 2007/0156117 | A1 | | 7/2007 | Adams et al. |
| 2008/0091146 | A1 | | 4/2008 | Solovay et al. |
| 2010/0022969 | A1 | | 1/2010 | Renaux |
| 2010/0113880 | A1 | | 5/2010 | Page |
| 2010/0185155 | A1 | * | 7/2010 | McMichael ......... A61J 15/0038 604/175 |
| 2010/0312192 | A1 | | 12/2010 | Fitzgerald et al. |
| 2011/0009828 | A1 | | 1/2011 | Prechtel et al. |
| 2011/0082442 | A1 | | 4/2011 | Solovay et al. |
| 2011/0144623 | A1 | | 6/2011 | Renaux et al. |
| 2011/0288534 | A1 | | 11/2011 | Aguirre et al. |
| 2011/0313359 | A1 | | 12/2011 | Cohen |
| 2012/0010571 | A1 | | 1/2012 | Adams et al. |
| 2012/0221032 | A1 | | 8/2012 | Duperier et al. |
| 2012/0277541 | A1 | | 11/2012 | Bhargava et al. |
| 2013/0158401 | A1 | * | 6/2013 | Evert ..................... A61B 8/48 600/439 |
| 2013/0165862 | A1 | | 6/2013 | Griffith et al. |
| 2014/0121658 | A1 | | 5/2014 | Cosman, Jr. et al. |
| 2014/0276628 | A1 | | 9/2014 | Gandras et al. |
| 2014/0330254 | A1 | | 11/2014 | Rosenberger et al. |
| 2015/0038794 | A1 | | 2/2015 | Pattison et al. |
| 2017/0367932 | A1 | | 12/2017 | Millis et al. |

FOREIGN PATENT DOCUMENTS

| | | |
|---|---|---|
| EP | 0824929 | 2/1998 |
| GB | 2243299 | 10/1991 |
| WO | WO 2010/075032 | 7/2010 |
| WO | WO 2010/115102 | 10/2010 |
| WO | WO 2014/203259 | 12/2014 |
| WO | WO 2016/103268 | 6/2016 |
| WO | WO 2017/109788 | 6/2017 |

OTHER PUBLICATIONS

International Preliminary Report on Patentability dated Dec. 30, 2015 From the International Bureau of WIPO Re. Application No. PCT/IL2014/050559.

Kentec Medical "Ameritus Entral™ Feeding Tubes", Kentec Medical, Inc., Premarket Notification, KI00526, 5 P., Apr. 22, 2010.

NeoMed "NeoMed Polyurethane Feeding Tube", NeoMed Inc., K082238, 5 P., Oct. 1, 2008.

Communication Pursuant to Article 94(3) EPC dated Mar. 6, 2017 From the European Patent Office Re. Application No. 14814409.0. (5 Pages).

Supplementary European Search Report and the European Search Opinion dated Feb. 7, 2017 From the European Patent Office Re. Application No. 14814409.0. (4 pages).

Office Action dated Aug. 22, 2017 From the State Intellectual Property Office of the People's Republic of China Re. Application No. 201480036964. (7 Pages).

Translation of Notification of Office Action dated Aug. 22, 2017 From the State Intellectual Property Office of the People's Republic of China Re. Application No. 201480036964. (3 Pages).

Communication Pursuant to Article 94(3) EPC dated Nov. 16, 2017 From the European Patent Office Re. Application No. 14814409.0. (4 Pages).

International Preliminary Report on Patentability dated Jul. 6, 2017 From the International Bureau of WIPO Re. Application No. PCT/IL2015/051252. (8 Pages).

International Search Report and the Written Opinion dated Mar. 29, 2017 From the International Searching Authority Re. Application No. PCT/IL2016/051377. (21 Pages).

International Preliminary Report on Patentability dated Jul. 5, 2018 From the International Bureau of WIPO Re. Application No. PCT/IL2016/051377. (14 Pages).

Restriction Official Action dated Jul. 6, 2018 From the US Patent and Trademark Office Re. U.S. Appl. No. 15/538,732. (5 pages).

Supplementary European Search Report and the European Search Opinion dated Jun. 15, 2018 From the European Patent Office Re. Application No. 15867972.0. (8 Pages).

Communication Pursuant to Article 94(3) EPC dated Aug. 31, 2018 From the European Patent Office Re. Application No. 14814409.0. (5 Pages).

Official Action dated Sep. 14, 2018 From the US Patent and Trademark Office Re. U.S. Appl. No. 15/538,732. (30 pages).

Official Action dated Dec. 5, 2018 From the US Patent and Trademark Office Re. U.S. Appl. No. 16/065,807. (22 pages).

Applicant-Initiated Interview Summary dated Jan. 23, 2019 From the US Patent and Trademark Office Re. U.S. Appl. No. 16/065,807. (4 pages).

Official Action dated May 3, 2019 From the US Patent and Trademark Office Re. U.S. Appl. No. 16/065,807. (23 pages).

Communication Pursuant to Article 94(3) EPC dated Jun. 11, 2019 From the European Patent Office Re. Application No. 15872106.8. (7 Pages).

International Search Report dated Oct. 21, 2014 From the International Searching Authority Re. Application No. PCT/IL2014/050559.

Written Opinion dated Oct. 21, 2014 From the International Searching Authority Re. Application No. PCT/IL2014/050559.

Notification of Office Action and Search Report dated Nov. 4, 2019 From the National Intellectual Property Administration of the People's Republic of China Re. Application No. 201580076812.7 and Its Translation of Office Action Into English. (18 Pages).

Applicant-Initiated Interview summary dated Apr. 24, 2019 From the US Patent and Trademark Office Re. U.S. Appl. No. 15/538,732.

(56) References Cited

OTHER PUBLICATIONS

Applicant-Initiated Interview Summary dated Apr. 24, 2019 From the US Patent and Trademark Office Re. U.S. Appl. No. 16/065,807. (3 Pages).
Official Action dated Sep. 20, 2019 From the US Patent and Trademark Office Re. U.S. Appl. No. 16/065,807. (25 pages).
Supplementary European Search Report and the European Search Opinion dated Jul. 19, 2019 From the European Patent Office Re. Application No. 16877906.4. (7 Pages).

\* cited by examiner

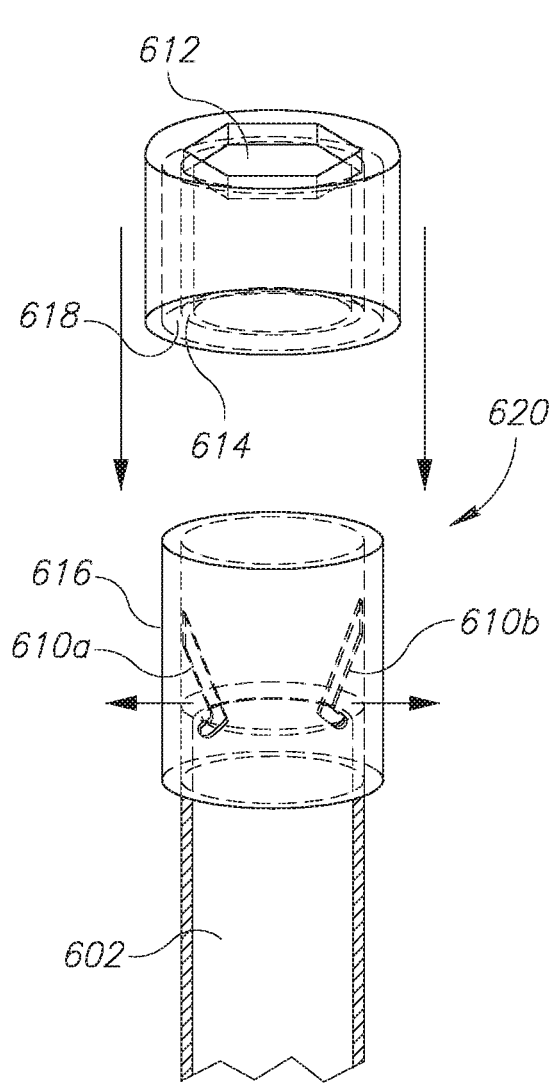
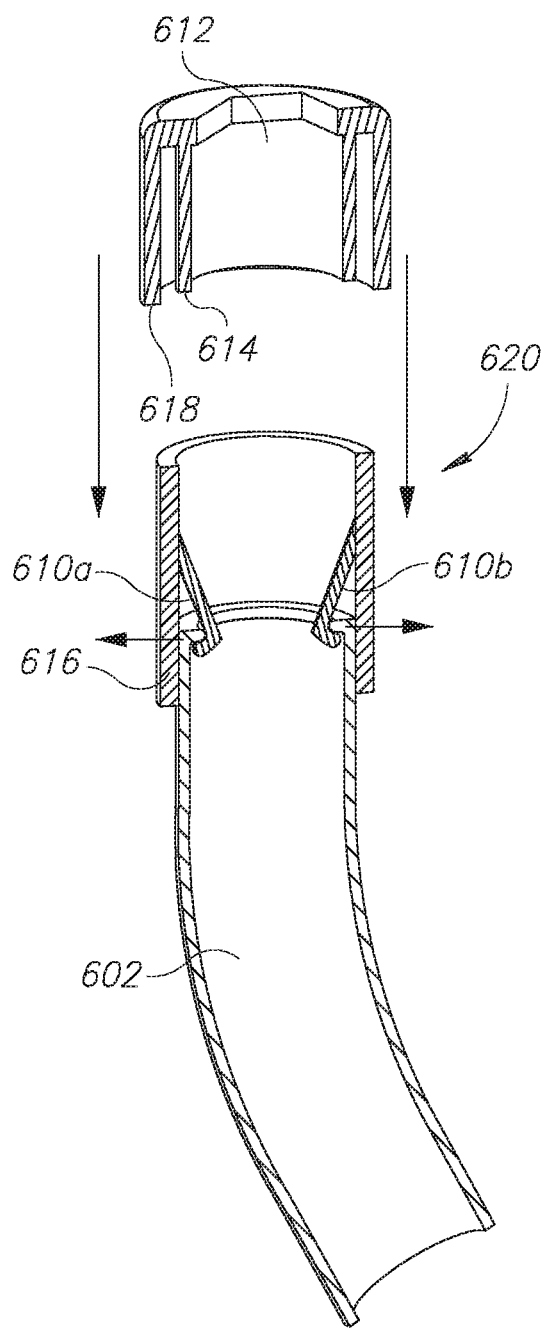
FIG.6A
FIG.6B

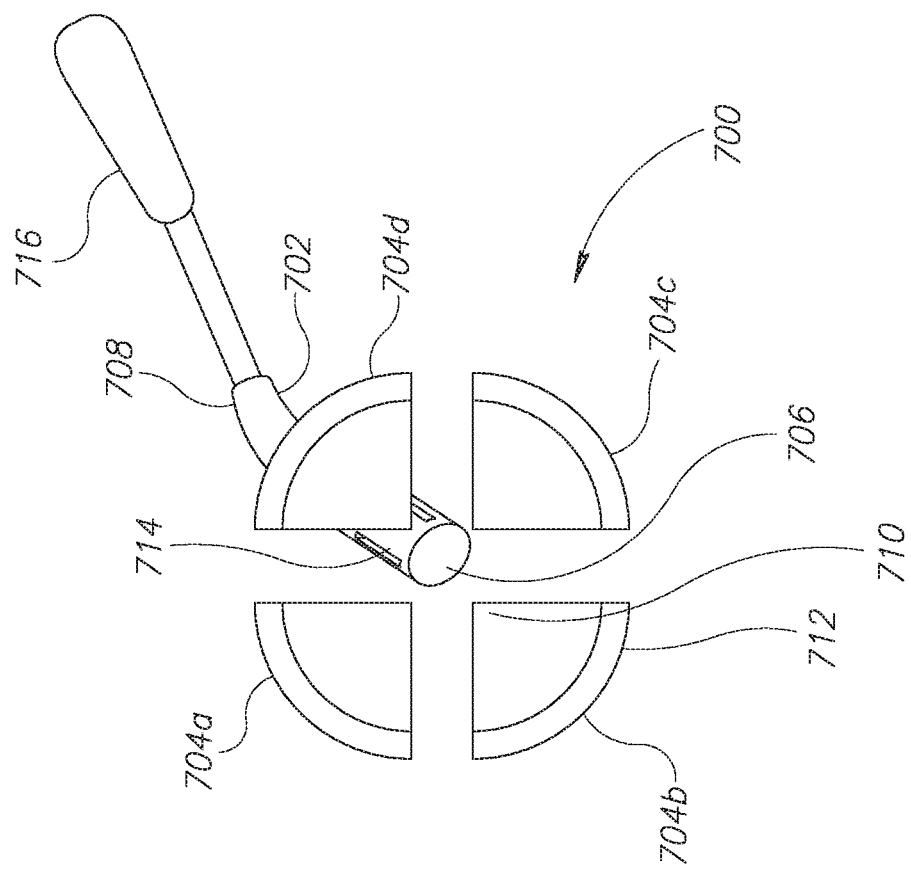
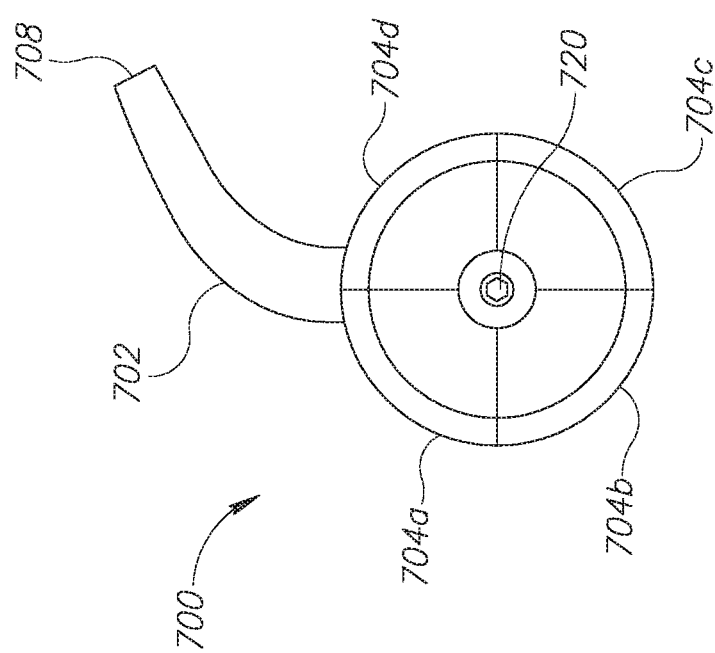
FIG.7B
FIG.7A

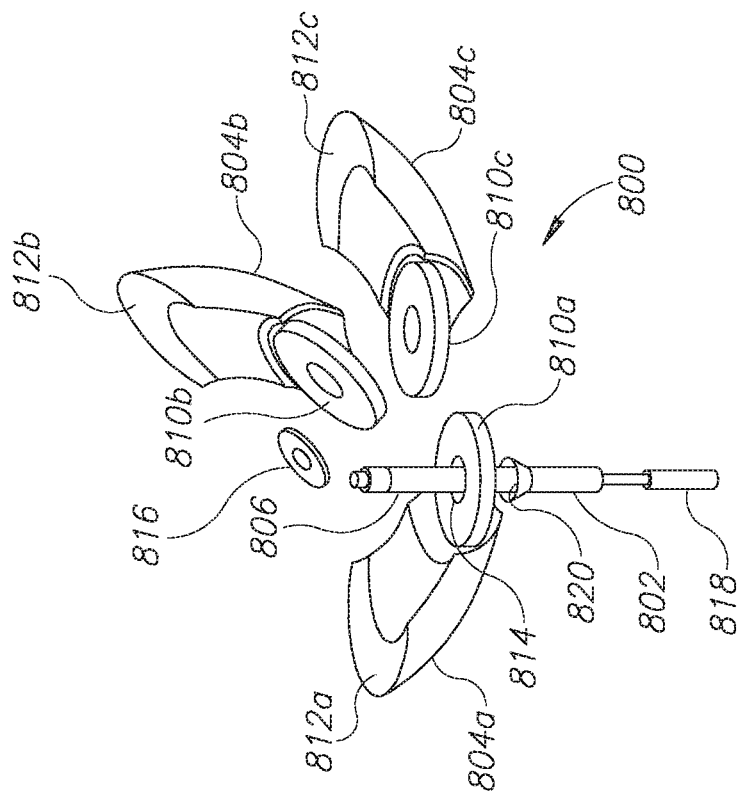
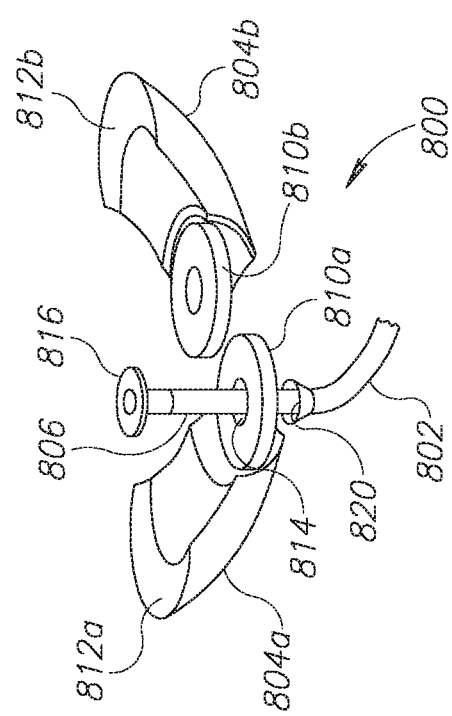
FIG.8B
FIG.8A

DEVICES AND METHODS FOR PERCUTANEOUS ENDOSCOPIC GASTROSTOMY AND OTHER OSTOMY PROCEDURES

RELATED APPLICATIONS

This application is a National Phase of PCT Patent Application No. PCT/IL2014/050559 having International filing date of Jun. 19, 2014, which claims the benefit of priority under 35 USC § 119(e) of U.S. Provisional Patent Application No. 61/837,184 filed on Jun. 20, 2013. The contents of the above applications are all incorporated by reference as if fully set forth herein in their entirety.

FIELD OF THE INVENTION

The present invention relates to devices and methods for percutaneous endoscopic gastrostomy (PEG) and other surgical procedures requiring formation of a stoma into a body lumen. More specifically, the present invention relates to ostomy tubes, such as PEG tubes, with improved retention means.

BACKGROUND OF THE INVENTION

Percutaneous endoscopic gastrostomy (PEG) is a medical procedure for placing a feeding tube through the abdominal wall and into the stomach of a patient, aided by endoscopy. PEG tubes are placed in a vast array of age-groups and disease-states to allow nutrition, fluids and/or medications to be put directly into the stomach, when oral intake is inadequate or not possible.

There are several techniques for performing PEG. In general, the procedure includes placing an endoscope into the patient's mouth and advancing it along the esophagus into the stomach. The endoscope allows viewing the stomach lining to determine the correct insertion site of the PEG tube, where a small incision is made in the abdominal wall. The procedure further includes inserting a guidewire and advancing the tube over the guidewire through the patient's mouth, esophagus, stomach and out through the abdominal wall. The PEG tube typically contains a retention means, both external and internal, to secure the tube in place and minimize accidental retraction and/or dislodgement.

There are several types of PEG tubes of different sizes and internal retention mechanisms. Examples include PEG tubes with internal mushroom-like soft and flexible bumper or bolster, PEG tubes with semi-rigid internal bumper that prevents their removal by external traction, and balloon-retained tubes where a balloon at the end of the tube positioned inside the stomach is inflated after insertion. The insertion of PEG tubes with a flexible or semi-rigid internal bumper is typically performed such that the end of the tube that is not engaged with the bumper is entered first, through the patient's mouth, and advanced in a retrograde manner along the guidewire and out the incision made in the abdominal wall until the retention bumper touches the internal wall of the stomach. The tube is then further secured using an external bolster affixed at the skin level. A schematic illustration of advancing a PEG tube with internal bumper (B) along a patient's esophagus is shown in FIG. 1A. Illustration of a PEG tube secured to the abdominal wall of a patient (externally and internally) is shown in FIG. 1B. Balloon-retained tubes are usually used when a tract has already been established in the abdominal wall. Such tubes can be inserted through the tract in a deflated form, and inflated when inside the stomach to secure the tube in place.

PEG tubes should be replaced regularly, typically every few months. Removal of PEG tubes (either for the placement of a new tube or in cases where enteral feeding is no longer required) can be performed by different methods, depending, inter alia, on the tube design. For example, mushroom-retained tubes can be removed by external retraction. Upon pulling, the internal flexible bumper folds and slides out through the tube tract. This technique typically causes considerable pain to the patient, and may result in complications such as perforation and peritonitis. As another example, PEG tubes with rigid internal bumpers can be removed by repeat gastroscopy and retrieval of the internal PEG bumper by the oral route. As this method requires repeat endoscopy, it is considered more complicated and costly. Another known method of PEG tube removal is the "cut and push" method (described, for example, in Kejariwal et al. 2009, *Nutr Clin Pract,* 24: 281), This method is generally applicable for PEG tubes with a rigid internal bumper, and involves cutting the tube at skin level and allowing the internal bumper to be expelled naturally. The "cut and push" method has several drawbacks. For example, the passage of the tube remnants and bumper through the gastrointestinal (GI) tract may cause bowel obstruction and/or perforation. The remnant tube "tail" might restrict free maneuvering of the bumper in the bowel, which is essential for proper extraction. In addition, the method is not recommended for certain patient populations, such as patients with previous abdominal surgery, known GI stricture and known motility disorders. In some cases, the insertion of a new, fresh tube entails another endoscopy.

Balloon-retained tubes can be removed by deflating the balloon. Although simple to operate, such tubes are considered less durable and more prone to tube complications, such as accidental dislodgment (see, for example, Funaki et al. 2001, *AJR,* 177(2); 359-362), which can be very hazardous in the 14 days after the insertion prior to mature tract formation (see, for example, Marshall et al. 1994, *J Clin Gastroenterol,* 18(3):210-2).

U.S. Pat. No. 4,795,430 discloses a device for intubating an ostomy, formed by a percutaneous endoscopic technique including a multi-lumen tube, having at least a fluid delivery lumen and an inflation lumen. The tube includes a port near one end to dispose the inflation lumen to ambient air and an outlet at another end to convey fluid from within the fluid lumen into a patient. A retention member, preferably an inflatable cuff, is joined near the other end of the tube and is inflatable and deflatable through the inflation lumen.

U.S. Pat. No. 5,112,310 discloses a gastrostomy tube which includes an elongated flexible wire guide and an elongated sleeve having a tapered end portion, the guide and sleeve having lengths sufficient to extend from a location outside the abdominal wall of the patient through the patient's stomach and esophagus and out the patient's mouth. The gastrostomy tube has a retention device in the form of an inflatable balloon or expandable and retractable cage adjacent an end portion for retaining the tube within the patient's stomach.

U.S. Pat. No. 5,391,159 discloses a gastrostomy tube which is a flexible tube having on one inner end thereof an improved energy absorbent internal retaining member. The energy absorbing internal retaining member has a hollow body portion with two resiliently reversible physical forms or shapes, toroidal-like, and, goblet-like connected to a foreshortened hollow axial stem portion that is attached to or integrally made with the inward end of the flexible tube. The internal retaining member is made in the toroidal-like form. During intentional removal, when under pressure against the stomach mucosa, the internal retaining member snaps into the unrolled, goblet-like shape and pulls smoothly out through the stoma tract.

U.S. Pat. No. 6,039,714 discloses an improved ostomy fluid tube and method for its use comprising a collapsible retention bolster for securing the tube to the inner stomach wall and fascia. The retention means comprise several resilient leaf or petal-shaped flanges circumferentially arranged about the feeding tube at a distal point thereon. The otherwise flat, circumferentially arranged flanges possess notches or grooves which facilitate collapse or folding of the retention means for easier removal through an ostomy or other internal cavity.

EP 2258334 discloses an apparatus for direct gastric feeding via a gastrostomy tract formed in a patient. The apparatus includes a tube, an internal bolster, an external bolster, and a force-generating device. The force-generating device may include a pair of automatically adjustable spring members on the external bolster. The spring members are responsive to changes in the length of the gastrostomy tract.

WO 2007/114880 discloses a surgical tool useful in performing percutaneous endoscopic gastrostomy and other surgical procedures requiring formation of a stoma into a body lumen. Such a tool would contain a first and second cannulae concentrically nested within one another and secured together at a distal end. An actuator is provided for selectively engaging and disengaging a retention mechanism located on that portion of the tool positioned within the body lumen. A locking mechanism is also provided to be used in conjunction with the retention mechanism for securing the cannulae to one another enabling the cannulae to be severed, and the actuator to be disposed, until the locking mechanism is disengaged upon formation and healing of an artificial stoma.

US 2011/0313359 discloses a gastrostomy tube including a retention device includes an elongated hollow shaft having a proximal first end and a distal second end and at least one retention member extending from the distal second end of the shaft. The at least one retention member moves between a retracted orientation and an open orientation.

There still remains a need for improved enteral feeding systems containing tubes and retention means which are easy to operate, durable and cost effective. In addition, there is a need for improved tubes for other ostomy procedures.

SUMMARY OF THE INVENTION

The present invention provides, according to some embodiments, gastrostomy tubing systems comprising gastrostomy tubes with improved retention structures. In particular, the present invention provides, according to some embodiments, gastrostomy tubing systems comprising gastrostomy tubes and dismantlable retention structures, such as dismantlable internal bolsters. In contrast to hitherto described retention structures, the improved retention structures disclosed herein can be separated and dismantled from the tube upon external manipulation, to facilitate simple and safe removal of the tube. The dismantlable retention structures disclosed herein are configured to engage with a gastrostomy tube and secure the gastrostomy tube to the inner wall of a subject's stomach and, when the tube is no longer needed, to disintegrate or disassemble from the tube upon external manipulation and be released from the tube, thereby the extraction of the tube is facilitated. The dismantled retention structure may be released into the stomach of a patient and expelled naturally from the body. The provided gastrostomy tubing systems therefore enable simple extraction of the gastrostomy tube, that can be performed without repeated endoscopy and with minimal patient discomfort.

The retention structure disclosed herein may be composed of a single element or a plurality of elements that can be disintegrated, or disassembled, upon external manipulation. According to some embodiments, a retention structure comprising a plurality of elements is configured to disassemble into separate elements upon external manipulation, to thereby dismantle from the tube and facilitate removal of the tube. The external manipulation may include, for example, mechanical, radiofrequency and/or magnetic forces. In some embodiments, the manipulation is applied through an internal lumen of the gastrostomy tube. The gastrostomy tubing systems disclosed herein further enable, according to some embodiments, to remove the gastrostomy tube only, while the retention structure is held inside the stomach, and to place a new, fresh tube instead of the removed tube. Thus, the provided gastrostomy tubing systems facilitate tube replacement while the internal retention structure remains in the stomach, thereby reducing costs and risks associated with hitherto described gastrostomy tubing systems.

The retention structures disclosed herein are typically formed as an "add-on" structure configured to be mounted on the tube. The one or plurality of elements may be configured to directly attach to the tube, or may be configured to attach to a central cylinder, that can then be mounted on the tube. The simple operation of the retention structures disclosed herein may minimize patient discomfort and reduce risks for potential complications.

According to one aspect, the present invention provides a gastrostomy tubing system comprising a gastrostomy tube comprising a distal end and a proximal end, the distal end is configured to be positioned in a stomach of a subject and the proximal end is configured to extend outside the subject's body; and a dismantlable retention structure connected to said distal end of said tube and configured to secure the tube to an inner wall of the stomach when the distal end is inside the stomach, and, when the tube is to be removed, to dismantle from said tube upon external manipulation and facilitate removal of the tube.

In some embodiments, the gastrostomy tubing system is configured to facilitate replacement of said tube while the dismantlable retention structure is held inside the stomach.

In some embodiments, the gastrostomy tubing system comprises a gripping member configured to associate with said tube and said dismantlable retention structure, said gripping member is operable to change from a first position in which it is associated with both dismantlable retention structure and tube, to a second position in which it grips the dismantlable retention structure while allowing release and replacement of the tube.

In some embodiments, the gripping member is further configured to change to a third position in which it allows dismantlable retention structure to dismantle from the tube and be released, and also allows removal of the tube.

The gripping member may include a single element or a plurality of elements.

In some embodiments, the gripping member is configured to engage with an external gripping tool configured for insertion through a lumen of said tube, to allow, when in the engaged position, to grip the dismantlable retention structure while allowing release and replacement of the tube.

In some embodiments, points of association of the gripping member to the dismantlable retention structure and tube are configured to be located inside the stomach.

In some embodiments, when points of association of the gripping member to the dismantlable retention structure and tube are configured to be located inside the stomach, the gripping member comprises one or more clamps and a removable plug. In some embodiments, the clamps are configured to reversibly grip a distal end of a tube configured to be positioned inside a subject's stomach in response to the operation of the plug. In some embodiments, the clamps are configured to reversibly grip the distal end of the tube upon change of the plug from a first position in which it engages with the clamps such that they grip the distal end of the tube, to a second position in which the plug disengages from the clamps such that they release the distal end of the tube and the tube can be removed.

In some embodiments, when points of association of the gripping member to the dismantlable retention structure and tube are configured to be located inside the stomach, the gripping member comprises a thread. In some embodiments, the thread is internal, namely, configured to be positioned inside the stomach, and is accessible from outside the body. In some embodiments, the internal thread is configured to engage with an external screwdriver, and allows gripping or release of a distal end of a tube in response to rotational motion of the screwdriver. In some embodiments, the internal thread is configured to enable, upon engagement with the screwdriver and upon application of rotational motion of the screwdriver, to change the configuration of the tubing system from a first position in which both the distal end of the tube and the retention structure are gripped, to a second position in which only the retention structure is gripped while removal of the tube is facilitated.

In some embodiments, when points of association of the gripping member to the dismantlable retention structure and tube are configured to be located inside the stomach, the gripping member comprises one or more cables. In some embodiments, the cables are configured to associate with dismantlable retention structure and tube inside the stomach and also to protrude and be accessible outside the body.

In some embodiments, a point of association of the gripping member to the dismantlable retention structure is configured to be located inside the stomach, and a point of association of the gripping member to the tube is configured to be located outside the body.

In some embodiments, when a point of association of the gripping member to the dismantlable retention structure is configured to be located inside the stomach, and a point of association of the gripping member to the tube is configured to be located outside the body, the gripping member comprises a mesh. In some embodiments, the mesh is configured to extend from an internal location inside the stomach, through the abdominal wall, to an external location outside the body. In some embodiments, the mesh is configured to engage with the retention structure inside the stomach at one end thereof, and with the distal end of the tube outside the body at an opposite end thereof.

In some embodiments, a point of association of the gripping member to the dismantlable retention structure is configured to be located inside the stomach, and a point of association of the gripping member to the tube is configured to be movable from a first position in which said point of association is inside the stomach, to a second position in which said point of association is outside the body.

In some embodiments, when a point of association of the gripping member to the dismantlable retention structure is configured to be located inside the stomach, and a point of association of the gripping member to the tube is configured to be movable from a first position in which said point of association is inside the stomach, to a second position in which said point of association is outside the body, the gripping member comprises a one or more strips. In some embodiments, the strips are configured for movement between inside the stomach and outside the body. In some embodiments, the strips are configured to engage with the retention structure at one end thereof, and with the distal end of the tube at an opposite end thereof. In some embodiments, the point of association with the retention structure is inside the stomach, and the point of association with the tube is configured to move between inside the stomach and outside the body in response to an external manipulation, such as operation of a tool inserted through the lumen of the tube In some embodiments, the dismantlable retention structure provided herein comprises a plurality of retention elements configured to disassemble upon external manipulation and thus dismantle from said tube.

In some embodiments, the retention elements are configured to assemble to the distal end of said tube by one or more removable plugs. In some embodiments, the retention elements are configured to assemble to the distal end of said tube by one or more removable, such as retractable, pins. In additional embodiments, the retention elements are configured to assemble to the distal end of said tube by one or more removable screw-nuts. In yet additional embodiments, the retention elements are configured to assemble to the distal end of said tube by one or more foldable elements. In yet additional embodiments, the retention elements are configured to assemble to the distal end of said tube by one or more cuttable or retractable sutures.

In some embodiments, the retention elements are configured to extend radially outwardly around the distal end of said tube In some embodiments, the retention elements are removably connected to each other.

According to another aspect, the present invention provides a dismantlable retention structure for a gastrostomy tube configured to connect to a distal end of the gastrostomy tube and secure the tube to an inner wall of a subject's stomach when the distal end is inside the stomach, and, when the tube is to be removed, to dismantle from said tube upon external manipulation and facilitate removal of the tube.

In some embodiments, the dismantlable retention structure is configured to facilitate replacement of a gastrostomy tube while being held inside the stomach.

In some embodiments, the dismantlable retention structure is configured to associate with a gripping member, the gripping member is configured to associate with a gastrostomy tube and said dismantlable retention structure and is operable to change from a first position in which it is associated with both dismantlable retention structure and tube, to a second position in which it grips the dismantlable retention structure while allowing release and replacement of the tube. In some embodiments, the dismantlable retention structure comprises the gripping member.

In some embodiments, the dismantlable retention structure comprises a plurality of retention elements configured to disassemble upon external manipulation and thus dismantle from said tube.

In some embodiments, the dismantlable retention structure comprises a central cylinder and a plurality of retention elements configured to removably assemble to said cylinder, wherein said plurality of retention elements are configured to disassemble from said central cylinder upon external manipulation.

In some embodiments, the retention elements are configured to extend radially outwardly around said cylinder. In some embodiments, the retention elements are removably connected to each other.

According to a further aspect, the present invention provides a kit for gastrostomy comprising: (i) a gastrostomy tubing system comprising a gastrostomy tube comprising a distal end and a proximal end, the distal end is configured to be positioned in a stomach of a subject and the proximal end is configured to extend outside the subject's body; a dismantlable retention structure connected to said distal end of said tube and configured to secure the tube to an inner wall of the stomach when the distal end is inside the stomach, and, when the tube is to be removed, to dismantle from said tube upon external manipulation and facilitate removal of the tube; and a gripping member configured to associate with said tube and said dismantlable retention structure, said gripping member is operable to change from a first position in which it is associated with both dismantlable retention structure and tube, to a second position in which it grips the dismantlable retention structure while allowing release and replacement of the tube; and a vimg tool configured for insertion through a lumen of said tube and engagement with the gripping member, to grip the dismantlable retention structure while allowing release and replacement of the tube.

In some embodiments, the kit further comprises a releasing tool configured for insertion through a lumen of said tube, said releasing tool is operable to dismantle the dismantlable retention structure from the tube to thereby facilitate release of the dismantlable retention structure and removal of the tube when the tube is no longer needed.

According to yet a further aspect, the present invention provides a method for performing gastrostomy in a subject in need thereof, utilizing gastrostomy systems as disclosed herein. In some embodiments, the method comprises inserting to the stomach of the subject a gastrostomy tube comprising a distal end and a proximal end, the distal end is configured to be positioned in the stomach and the proximal end is configured to extend outside the subject's body, said tube is having a dismantlable retention structure connected to said distal end of said tube, said dismantlable retention structure is configured to secure the tube to an inner wall of the stomach when the distal end is inside the stomach, and, when the tube is to be removed, to dismantle from said tube upon external manipulation and facilitate removal of the tube.

According to yet a further aspect, the present invention provides a method for performing gastrostomy in a subject in need thereof, said method comprising: (i) providing a dismantlable retention structure for a gastrostomy tube, said dismantlable retention structure is configured to connect to a distal end of the gastrostomy tube and secure the tube to an inner wall of a subject's stomach when the distal end is inside the stomach, and, when the tube is to be removed, to dismantle from said tube upon external manipulation and facilitate removal of the tube; and (ii) connecting said dismantlable retention structure to a distal end of a gastrostomy tube inserted into the stomach of said subject In some embodiments, the dismantlable retention structure comprises a plurality of retentionelements configured to disassemble and facilitate removal of said tube.

In some embodiments, the methods further comprise replacement of the gastrostomy tube by inserting a gripping tool through the lumen of said tube, said gripping tool is configured and operable to grip the dismantlable retention cture while allowing release and replacement of the tube.

In some embodiments, the methods further comprise removal of the gastrostomy tube by inserting a releasing tool through the lumen of said tube, said releasing tool is configured and operable to dismantle the dismantlable retention structure from the tube to thereby facilitate release of the dismantlable retention structure and removal of the tube.

The present invention further provides an ostomy tubing system comprising an ostomy tube comprising a distal end and a proximal end, the distal end is configured to be positioned in a body lumen of a subject and the proximal end is configured to extend outside the subject's body; and a dismantlable retention structure connected to said distal end of said tube and configured to secure the tube to an inner wall of the body lumen when the distal end is inside the body lumen, and, when the tube is to be removed, to dismantle from said tube upon external manipulation and being retrieved, to facilitate removal of the tube.

In some embodiments, the ostomy system is for use with a gastrointestinal tube, a thoracic tube, an abdominal tube or a bladder tube. Each possibility represents a separate embodiment of the invention.

As noted above, according to some embodiments, retention elements that constitute a dismantlable retention structure configured for use with a gastrostomy tube may be assembled to one end of the gastrostomy tube (a distal end of the tube configured to be positioned inside the stomach) by several mechanisms. For example, by one or more removable plugs, one or more removable, such as retractable, pins, and/or one or more removable screw-nuts or folding elements. As another example, the retention elements may be secured to the tip of the tube through one or more sutures that can be cut or retracted to allow disassembly and release of the retention elements.

In some embodiments, assembly of said plurality of retention elements is mediated through at least one removable pin and/or removable screw-nut.

In other embodiments, assembly of said plurality of retention elements is mediated through cuttable sutures. In additional embodiments, assembly of said plurality of retention elements is mediated through retractable sutures.

In some embodiments, said one end of said tube comprises a plurality of grooves cut therein, each groove is configured to accommodate at least one of the plurality of retention elements through a proximal end of said retention elements.

In some embodiments, a proximal end of each of said plurality of retention elements is configured to be accommodated within at least one of said grooves. In some embodiments, each of the plurality of said retention elements comprises a tapered proximal end sized to, and configured for, accommodation within said groove.

In some embodiments, the plurality of retention elements are configured to be fixed to said plurality of grooves through at least one removable pin, wherein removal of said pin disassembles the plurality of retention elements from said grooves. The disassembled retention elements are then released into the stomach of the patient. In some embodiments, the retention elements are configured to be assembled by one pin. In other embodiments, the retention elements are configured to be assembled by more than one pin.

In some embodiments, the pin is configured to be released by a screwdriver inserted through a lumen of said tube. Thus, in some embodiments, the tube comprises at least one lumen configured for insertion of a screwdriver therethrough, for removing at least one pin connecting said plurality of retention elements.

In some embodiments, said one end of said tube comprises one or more circumferential apertures, each aperture is configured to enable threading at least one suture therethrough, said at least one suture is configured to connect at least one of said plurality of retention elements to said tube.

In some embodiments, each of said plurality of retention elements comprises one or more apertures, each aperture is configured to enable threading at least one suture therethrough, to connect said retention element to said tube. In some particular embodiments, said one or more apertures are located at a proximal end of said retention elements.

In some embodiments, the at least one suture is configured to be cut by a cutting tool inserted through a lumen of said tube, According to these embodiments, a portion of the suture is accessible from the internal lumen of said tube.

Thus, in some embodiments, the tube comprises at least one lumen configured for insertion of a cutting tool therethrough, for cutting at least one suture connecting said plurality of retention elements. Cutting the sutures disassembles the plurality of retention elements from said tube. The disassembled retention elements may then be released into the stomach of the patient.

In some embodiments, each of said plurality of retention elements comprises a rounded proximal end having a central bore cut therein, said proximal end is configured for threading onto said one end of said tube. In some embodiments, said one end of said tube comprises a support base configured to mount thereon said plurality of retention elements. In some embodiments, the retention elements are configured to be mounted on said support base fixed to the tip of the tube by at least one removable screw-nut.

In some embodiments, the plurality of retention elements are further configured to connect to each other in a reversible manner.

In some embodiments, disassembly of the retention elements from the tube is performed simultaneously to their disassembly from each other.

In some embodiments, the plurality of retention elements are enclosed within an envelope (e.g. a flexible envelope, such as a bag) and configured to be released upon opening of said envelope. According the these embodiments, a retention structure may be provided, said retention structure comprises a flexible envelope containing therein a plurality of spheres or beads, said plurality of spheres or beads are configured to be released upon opening of said envelope. The beads may be free or connected to one another (e.g., via sutures). In some embodiments, said envelope is configured to be opened up upon external manipulation.

The plurality of retention elements may be released into the stomach of the patient upon opening of the envelope. For example, in some embodiments, the envelope comprises at least one plug at a distal end thereof, wherein removal of said plug facilitates opening of said envelope. The retention elements contained within said envelope are then released into the stomach of the patient. In some embodiments, the plug is configured to be released by a tool inserted through a lumen of said tube.

Alternatively or additionally, the plurality of retention elements may be retrieved, or released back into the tube and collected outside the body of the patient. For example, in some embodiments, the retention structure comprises at least one wall separating an inner lumen of said envelope from an inner lumen of said tube. Upon removal of said at least one wall, the retention elements contained within the envelope are released into the lumen of the tube and may be collected outside the body of the patient. In some embodiments, the at least one wall is configured to be removed by a tool inserted through the lumen of said tube.

Such release mechanism, where the retention elements are released back into the tube, may be suitable for surgical ostomy procedures performed in closed cavities, including but not limited to the thoracic and abdominal cavities.

Thus, according to additional embodiments, the present invention provides multi-element retention structures and tubes comprising same, for use in thoracostomy and ostomy of the abdominal cavity.

Known retention structures comprising a flexible envelope typically contain gas or fluid within the envelope. Any minor damage or perforation of the envelope may result in gas or fluid leak from the envelope in contrast, the retention structure disclosed herein comprises a flexible envelope containing therein beads or spheres, that may remain within the envelope in the case of minor damages. It therefore provides durable, safe means for retention of ostomy tubes.

According to additional embodiments, the present invention provides a retention structure for a gastrostomy tube, said retention structure is configured to be released from the tube in its entirety upon external manipulation and facilitate removal of the tube. In some embodiments, the external manipulation includes mechanical manipulation. In additional embodiments, the external manipulation includes radiofrequency manipulation. In yet additional embodiment, the external manipulation includes magnetic manipulation.

In some embodiments, the manipulation is applied through an internal lumen of the gastrostomy tube.

Known methods for releasing a retention structure attached to a PEG tube in its entirety into the stomach of patient typically include cutting the tube at skin level. As a result, the retention structure is released together with the distal portion of the tube that extends into the patient's stomach. In contrast, the retention structure disclosed herein is separated from the tube and then released into the patient's stomach, thereby minimizing the risk of blockage and other complications.

In some embodiments, the retention structure comprises: (i) a dismantable retention element comprising a bore configured for the passage of a tube therein, said dismantable retention element is configured to be slidably mounted over a tip of said tube protruding into a body lumen of a subject following its insertion into said body lumen, and when the tube is no longer needed to disassemble from the tube upon external manipulation and be released into said body lumen; and (ii) a non-dismantable resilient retention element configured to be affixed to a tip of a tube, and further configured to fold upon external manipulation of the tube.

In some embodiments, the non-dismantable resilient retention element is configured to fold upon retraction of the tube. The non-dismantable resilient retention element is typically configured to fold such that in its folded configuration its can pass through the bore of the dismantable retention element.

Such a retention structure is suitable for ostomy procedures of the gastrointestinal tract. Thus, according to these embodiments, the body lumen is lumen of the gastrointestinal tract. According to these embodiments, when the tube is in use, the two retention elements secure the tube in place and minimize or even prevent its accidental removal. When the tube is no longer needed, the tube may be retracted. Upon retraction of the tube from the outside, the non-dismantable retention element may be folded, thereby enabling the removal of the tube. The presence of the dismantable retention element reduces the pressure that is applied to the inner wall of the gastrointestinal tract, thus alleviating or even preventing patient discomfort. Upon retraction of the tube and non-dismantable retention element, the dismantable retention element is released into the gastrointestinal tract and may be expelled naturally.

In some embodiments, the dismantable retention element comprising a bore is a rounded element configured to surround the tube.

In some embodiments, the non-dismantable resilient retention element is a mushroom-like shaped element secured to the tip of the tube.

In some embodiments, the non-dismantable retention element is made from a more flexible, resilient material compared to the dismantable retention element, which is made from a more rigid material.

The non-dismtantable retention element may be mounted or inserted over the tip of the tube. Alternatively, the non-dismtantable retention element may be formed as integral part of the tube.

These and further aspects and features of the present invention will become apparent from the figures, the detailed description, examples and claims which follow.

BRIEF DESCRIPTION OF THE FIGURES

FIG. 6A is a schematic illustration of a perspective of a gripping member and tube according to some embodiments of the present invention; FIG. 6B is a schematic illustration of a longitudinal cross-sectional view of a gripping member and tube according to some embodiments of the present invention.

FIGS. 7A-7B are schematic illustrations of perspective views of a gastrostomy tube and retention structure according to some embodiments of the present invention.

FIGS. 8A-8B are schematic illustrations of perspective views of a gastrostomy tube and retention structure according to additional embodiments of the present invention.

DETAILED DESCRIPTION OF THE INVENTION

The present invention is directed, inter alia, to gastrostomy tubing systems comprising gastrostomy tubes having improved retention structures. In contrast to hitherto described retention structures, the improved retention structures disclosed herein can be separated and dismantled from the tube upon external manipulation, to facilitate simple and safe removal of the tube. Advantageously, the tube and retention structure disclosed herein can be separated and removed without the need for endoscopy and with minimal patient discomfort. In some embodiments, the gastrostomy tubing systems provided herein facilitate multiple tube replacements with a single retention element that can be held in the stomach while tubes are replaced. When the tubing system is no longer needed, the retention structure can be released from the tube (e.g., the stomach) and the tube can be simply extracted.

Although typically referring to percutaneous endoscopic gastrostomy, the device may also be used in surgical astrostomy insertion. In addition, the device may also be used in ostomy procedures in the digestive system other than gastrostomy. Noel limiting examples of additional gastrointestinal ostomy procedures that may utilize the tubes and retention structures disclosed herein include jejunostomy, colonostomy, ileostomy.

The retention structure provided herein comprises, in some embodiments, a central axes and a plurality of removably assembled retention elements configured to disassemble upon external manipulation. In some embodiments, the retention elements are configured to extend radially outwardly around said axes.

In some embodiments, the gastrostomy tube provided herein comprises a first end, a second end and at least one lumen extending between said first and second ends; and a retention structure adjacent to the said first end of the tube, said retention structure comprises a plurality of retention elements extending radially outwardly around a center of said retention structure and being reversibly integrated thereto.

The retention structures disclosed herein are typically formed as an "add-on" structure configured to be mounted on the tube. The one or plurality of elements may be configured to directly attach to the tube, or may be configured to attach to a central cylinder, that can then be mounted on the tube.

In some embodiments, the tube and retention structure are assembled together prior to insertion into a subject. For example, in endoscopic procedures, pre-formed or pre-associated tube and retention structure can be inserted and placed in position by advancing the tube containing the retention structure at one end thereof over a guidewire, as known in the art. Alternatively, in surgical procedures for example, the retention structure may be attached to the tip of the tube following incision, as known in the art.

The "subject" (used herein interchangeably with "patient") according to embodiments of the present invention is a mammal, typically a human.

Figure 1A:
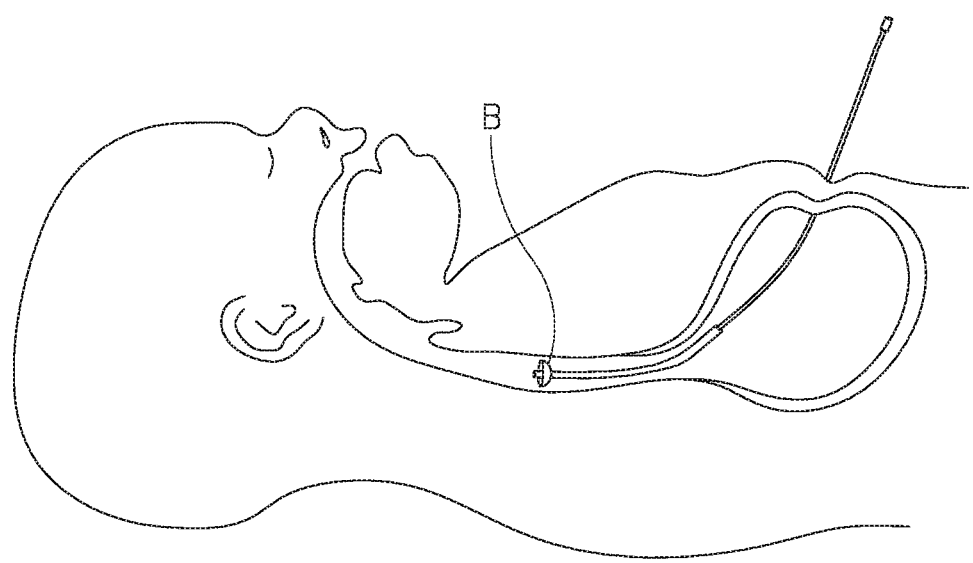
FIG. 1A is a schematic illustration of gastrostomy tube advancement along a patient's esophagus during percutaneous endoscopic gastrostomy (PEG) procedure.
Figure 1B:
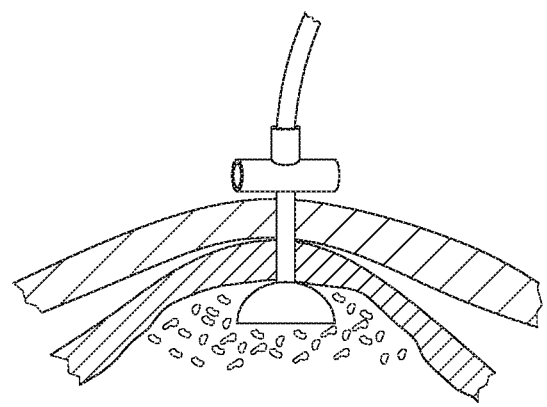
FIG. 1B is a schematic illustration a PEG tube secured to an abdominal wall of a patient (externally and internally).
Figure 2:
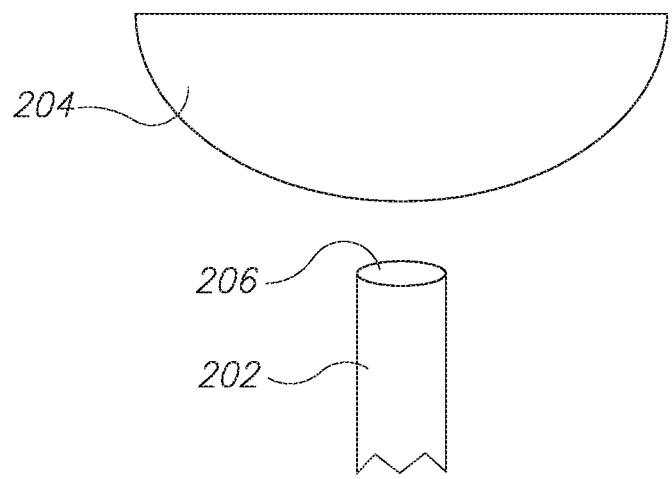
FIG. 2 is a schematic illustration of a gastrostomy tubing system according to some embodiments of the present invention.
Figures 3A, 3B:
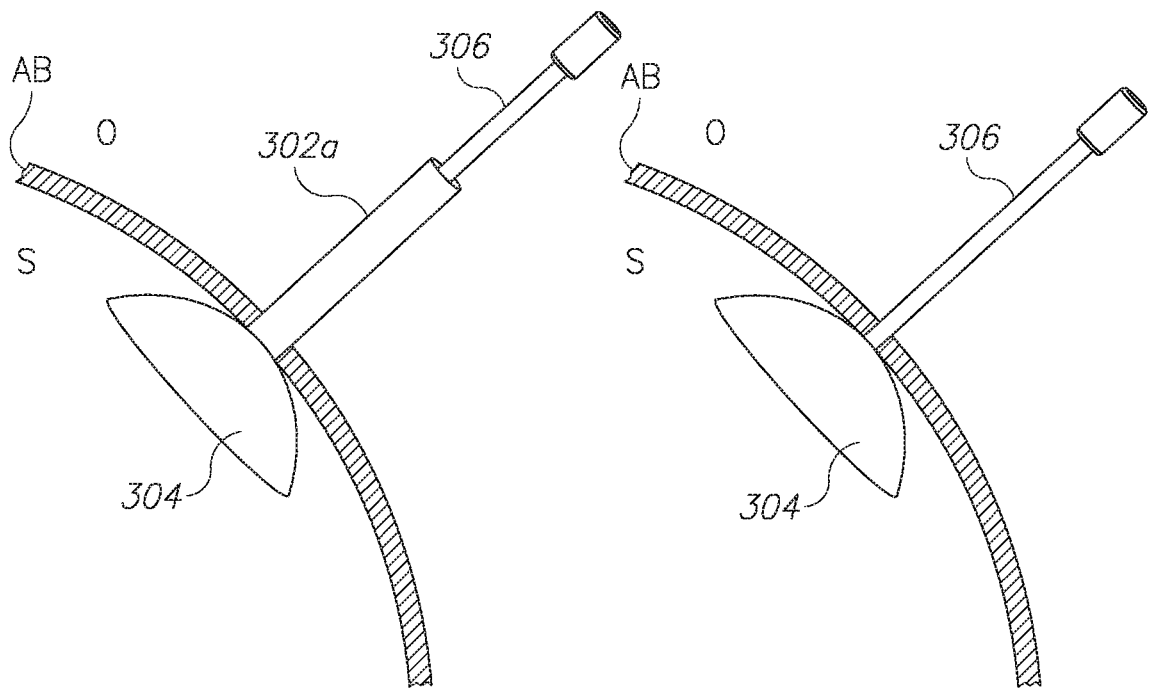
FIGS. 3A-D are simplified illustrations of tube replacement and removal procedures using a gastrostomy tubing system according to some embodiments of the present invention.
Figures 3C, 3D:
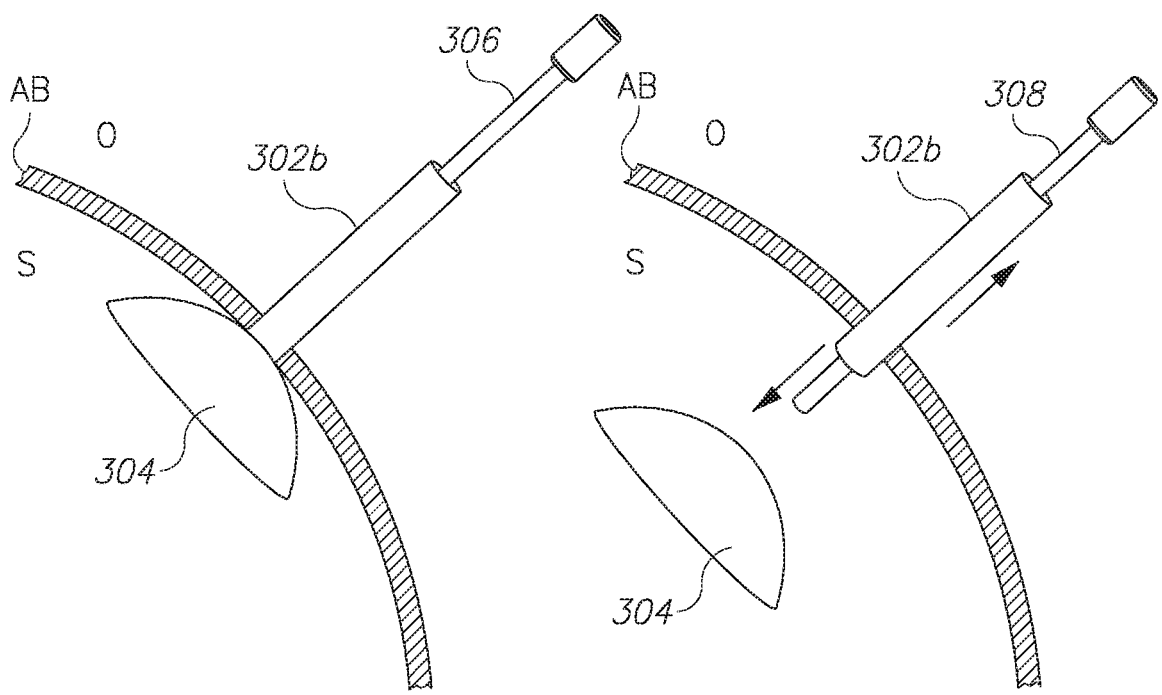

Reference is now made to FIG. 2, which is a schematic illustration of a gastrostomy tubing system according to some embodiments of the present invention. The tubing system comprises a tube (202) having a distal end (206) configured to be positioned in a stomach of a subject, and a proximal end configured to extend outside the subject's body. Distal end (206) is configured to engage with a dismantlable retention structure (204).

Dismantlable retention structure (204) is configured to engage with distal end (206) and secure tube (202) to an inner wall of the stomach when the distal end is inside the stomach, and, when tube (202) is to be removed, to dismantle from tube (202) upon external manipulation and facilitate removal of the tube. In the illustrated embodiment dismantlable retention structure (204) is a single element. In other embodiments, the dismantlable retention structure may comprise a plurality of elements configured to disassemble and thus dismantle from the tube.

Reference is now made to FIGS. 3A-D, which show a simplified illustration of tube replacement and removal procedures using a gastrostomy tubing system according to some embodiments of the present invention.

Stage A (FIG. 3A) shows a first gastrostomy tube (302a) with its distal end positioned inside a subject's stomach (S) and connected to an internal dismantlable retention structure (304). Dismantlable retention structure (304) contacts an inner wall of the stomach (S) and secures first tube (302a) to the inner wall of the stomach. The proximal end of first tube (302a) extends outside (O) the subject's body, through the abdominal wall (shown schematically as AB). A gripping member (not shown) can be associated with, and connect, dismantlable retention structure (304) and first tube (302a).

Stage A further shows a gripping tool (306) inserted into a lumen of first tube (302a). At stage A, gripping tool (306) is operated to grip dismantlable retention structure (304) while allowing the release of first tube (302a). For example, gripping tool (306) can engage with the gripping member and change the configuration of the gripping member from a first configuration in which it is associated with both dismantlable retention structure and tube, to a second configuration in which it grips the dismantlable retention structure while allowing release and replacement of the tube.

Stage B (FIG. 3B) shows the tubing system after removal of the first tube. Gripping tool (306) holds dismantlable retention structure (304) inside the stomach, and allows the placement of a second tube at the next stage.

Stage C (FIG. 3C) shows the tubing system after placement of a second tube (302b). Stage C shows second tube (302b) placed over gripping tool (306) and connected to dismantlable retention structure (304). At stage C, gripping tool (306) is operated to fasten second tube (302b) to dismantlable retention structure (304). After fastening, gripping tool (306) can be removed, leaving second tube (302b) connected to dismantlable retention structure (304), secured in place to the inner wall of the stomach.

Stages A-C can be repeated each time tube replacement is needed. When the tube is no longer needed (for example, when enteral feeding is no longer needed), Stage D is performed to remove the tube and release dismantlable retention structure (304). Stage D (FIG. 3D) shows the tubing system after dismantlable retention structure (304) is dismantled from second tube (302b). At stage D, a releasing tool (308) is inserted to the lumen of second tube (302b) and operated to dismantle dismantlable retention structure (304) from second tube (302b). It is noted that releasing tool and gripping tool can be the same tool, or two different tools. Each possibility represents a separate embodiment of the present invention. Non-limiting examples of gripping and/or releasing tools include screwdrivers of various types and cutting tools.

Dismantlable retention structure (304) is then released into the stomach (S) and expelled naturally. Second tube (302b) is pulled out through the abdominal wall (AB). In the illustrated embodiment, dismantlable retention structure (304) is a single element. In other embodiments, the dismantlable retention structure may comprise a plurality of elements configured to disassemble and thus dismantle from the tube.

Figure 4A:
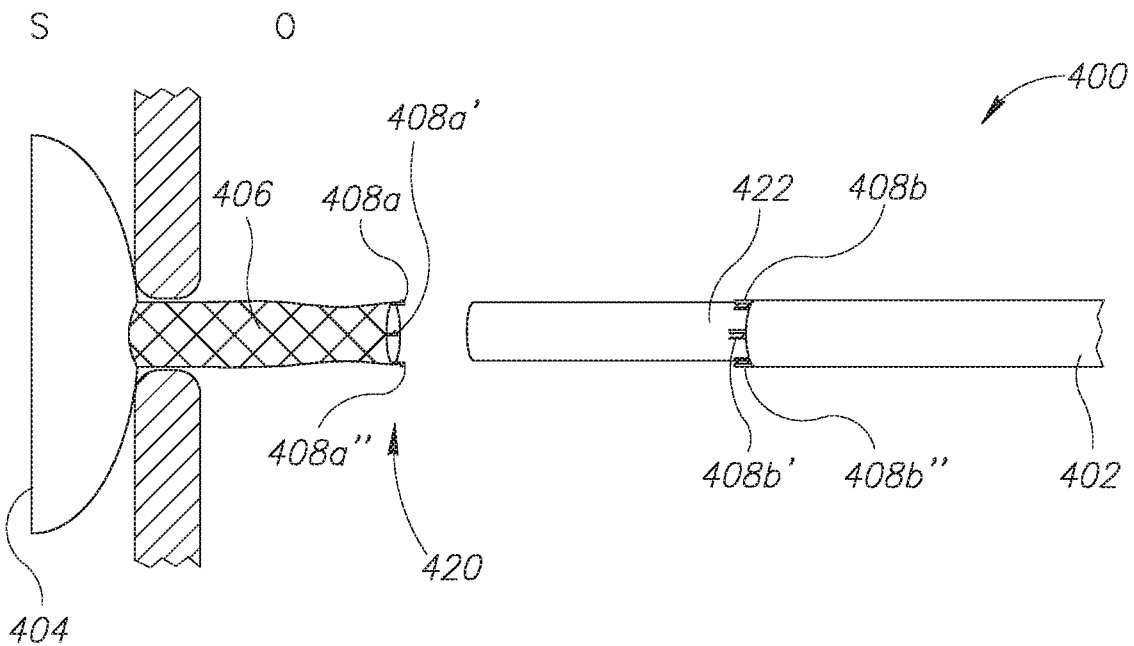
FIG. 4A and FIG. 4B are schematic illustrations of tubing systems comprising a gripping member according to some embodiments of the present invention.
Figure 4B:
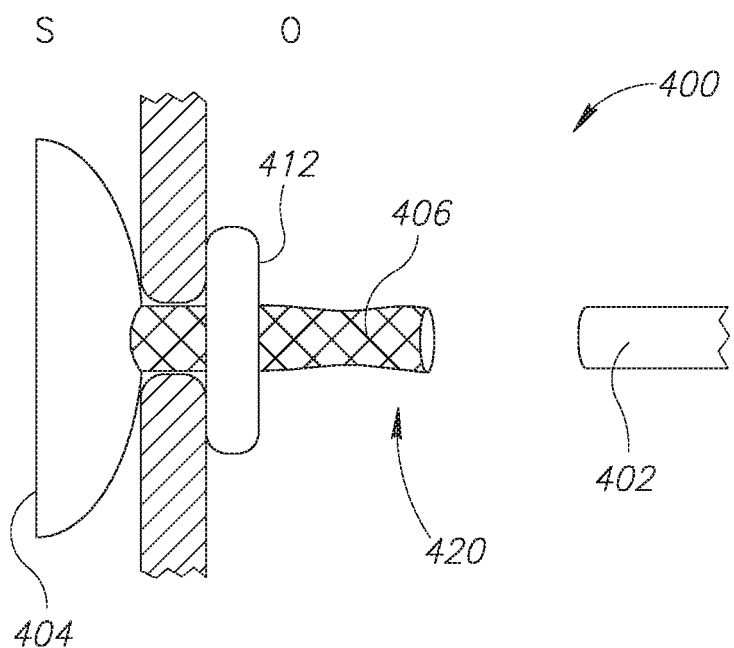
Figure 5A:
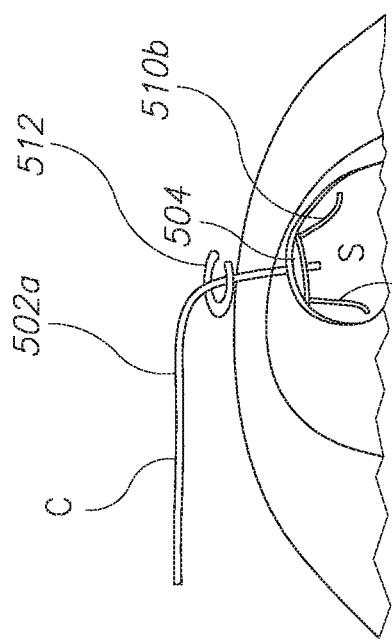
FIGS. 5A-E are a schematic illustration of a method of tube replacement using a tubing system comprising a gripping member according to some embodiments of the present invention.
Figure 5B:
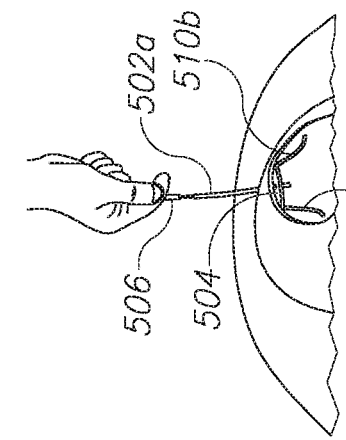
Figure 5C:
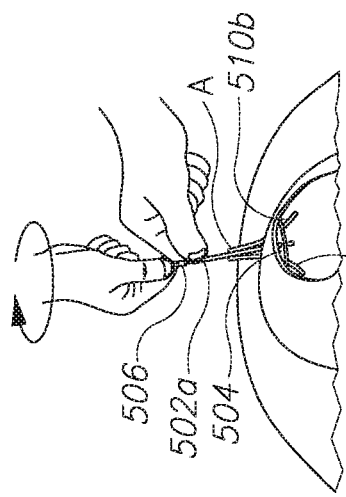
Figure 5D:
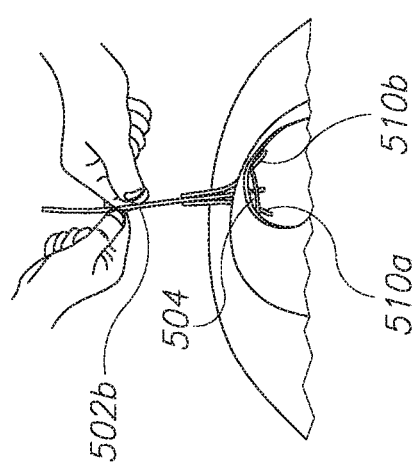
Figure 5E:
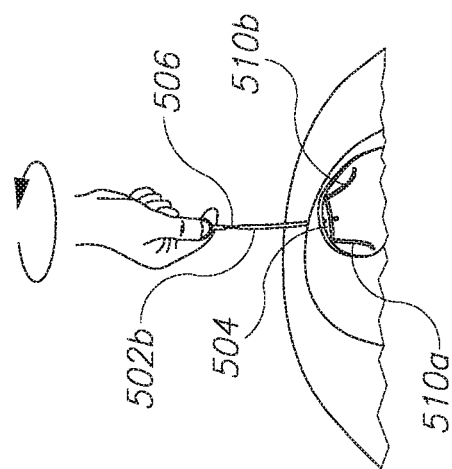

Reference is now made to FIGS. 4A-4B which show schematic illustrations of a tubing system comprising a gripping member according to some embodiments of the present invention.

Tubing system (400) comprises a tube (402), a dismantlable retention structure (404) and a gripping member (420). Tube (402) and dismantlable retention structure (404) are shown in a dissociated form.

The illustrated gripping member (420) comprises a mesh (406). Mesh (406) is highly flexible and made from a biocompatible, non-absorbable material, including for example silk, polypropylene, polyester, nylon and the like. Mesh (406) may include a protective coating to prevent granulation on or around the mesh, Mesh (406) may include both external and internal coating. Mesh (406) is connected at one end thereof to dismantlable retention structure (404). The point of association (point of contact/connection) of mesh (406) and dismantlable retention structure (404) is inside the stomach (S). An opposite end of mesh (406) extends through the abdominal wall and outside the body (O). The portion of mesh (406) that protrudes outside the body is configured to associate and accommodate a distal end (422) of tube (402). The point of association of mesh (406) and tube (402) is outside the body.

In FIG. 4A, gripping member (420) further comprises clips (408a, 408a', 408a") configured to connect to matching clips (408b, 408b', 408b") on tube (402). In FIG. 4A, distal end (422) of tube (402) has a diameter which is smaller than the diameter of the tube body. Distal end (422) is configured to fit within mesh (406). Distal end (422) is operable to be inserted into mesh (406) and pushed until clips (408b, 408b', 408b") of tube (402) are engaged with the matching clips (408a, 408a', 408a") of mesh (406). The length of distal end (422) is such that when clips (408b, 408b', 408b") are engaged with clips (408a, 408a', 408a"), distal end (422) protrudes inside the stomach (and associates with dismantlable retention structure (404)). When tube (402) is in need for replacement or removal, clips (408a, 408a', 408a") and clips (408b, 408b'. 408b") are operable to disengage, to facilitate retraction and release of the tube. A new tube, comprising matching clips, can be connected to mesh (406) (and accordingly to dismantlable retention structure (404)) instead of the removed tube. Mesh (406) can be held by a clinical practitioner during tube replacement to prevent release of mesh (406) and dismantlable retention structure (404) into the stomach. Alternatively, in case enteral feeding is no longer required, mesh (406) and dismantlable retention structure (404) can be released into the stomach and be expelled naturally. The high flexibility of mesh (406) (more flexible than a tube) enables smooth passage of dismantlable retention structure (404) along the gastrointestinal tract after release from tube (402) and thus minimizes a risk of obstruction and/or perforation.

In FIG. 4B, mesh (406) is operable to engage a distal end of tube (402). A distal end of tube (402) is pushed through mesh (406) until it associates with dismantlable retention structure (404) and protrudes inside the stomach. Tube (402) and mesh (406) are designed such that firm association is formed between them to avoid accidental dislodgement. Following insertion of tube (402), an external bolster (412) is mounted at the skin surface to secure tube (402) in place. External bolster (412) comprises a central bore (not visible in this figure) configured for accommodating tube (402) in association with mesh (406). When tube (402) is in need for replacement or removal, external bolster (412) can be removed and tube (402) can be retracted from mesh (406). A new tube can be connected to dismantable retention structure (404) instead of the removed tube. Alternatively, in case enteral feeding is no longer required, mesh (406) and dismantable retention structure (404) can be released into the stomach and be expelled naturally.

In other embodiments, the dismantable retention structure is meshed as well. According to these embodiments, release of the dismantable retention structure can be performed by cutting the mesh, thus disassemble the retention structure and dismantle it from the gastrostomy tube. The dismantled retention structure is then released into the stomach and can be expelled naturally. In some embodiments, the mesh and dismantable retention structure are woven such that cutting the mesh at one point unpicks or unstitches the entire meshed structure, causing mesh and dismantable retention structure to disintegrate into multiple elements and be released into the stomach.

Reference is now made to FIGS. 5A-5E which show a schematic illustration of a tubing system comprising a gripping member according to some embodiments of the present invention, and a method of tube replacement using such tubing system. In the illustrated embodiments, the tubing system comprises a tube (502), a dismantable retention structure (504) and a gripping member comprising two movable strips (510 a, b). Strips (510a,b) are configured to associate with both tube (502) and dismantable retention structure (504). The point of association of strips (510a,b) with dismantable retention structure (504) is inside the stomach (S) (not visible in the figures). The point of association of strips (510a,b) with tube (504) is movable from a first position inside the stomach to a second position outside the body, by an external manipulation.

Stage A of the illustrated tube replacement procedure (FIG. 5A) shows a partially cut away view of the gastrostomy tubing system in use in a subject. The tubing system comprises a first gastrostomy tube (502a) with its distal end positioned inside the stomach (S) and associated with an internal dismantable retention structure (504). Dismantable retention structure (504) contacts an inner wall of the stomach (S) and secures first tube (502a) to the inner wall of the stomach. The illustrated tubing system further comprises strips (510a,b). In the illustrated embodiments, distal ends of strips (510 a,b) protrude outside dismantable retention structure (504), into the stomach lumen.

The illustrated tubing system further comprises an external bolster (512) securing first tube (502a) at the skin level. When first tube (502a) is in need for replacement, the tube is cut at the point designated as (C), to allow insertion of a gripping tool into the lumen of the tube at the next stage.

At stage B (FIG. 5B), external bolster (512) is removed (stage B shows the tubing system after removal of the external bolster) and a gripping tool (506) is inserted into the lumen of first tube (502a). First tube (502a) is shown after a portion of the tube was cut away at the previous stage.

At stage C (FIG. 5C), gripping tool (506) is operated, for example, rotated, to cause movement of strips (510a,b) such that first tube (502a) disengages from dismantable retention structure (504) and is pulled upwards, outside the body. First tube (502a) is pulled until the point of association of strips (510a,b) and first tube (502a), designated as (A), is visible and accessible outside the body. Strips (510 a,b) remain associated with dismantable retention structure (504) while first tube (502a) is pushed outside the body.

Thus, point of association (A) between strips (510 a,b) and tube (502a) is moved from a first position in which it is inside the stomach, to a second position in which it is outside the body, thus allowing convenient and simple replacement of first tube (502a), outside the body, while dismantable retention structure (504) is held inside the stomach. At stage D (FIG. 5D), the first tube is operated to dissociate from strips (510 a,b).

Next, a second tube (502b) is placed over gripping tool (506) and operated to associate with strips (510 a,b). Dismantable retention structure (504) remains associated and held by strips (510 a,b) and gripping tool (506) while the first tube is replaced with second tube (502b).

At stage E (FIG. 5E), gripping tool (506) is operated, for example rotated in the opposite direction, such that the movement of strips (510 a,b) pushes second tube (502b) downwards, towards the stomach, until it engages with dismantable retention structure (504). When dismantable retention structure (504) and second tube (502b) are securely engaged, an external bolster can be affixed at the skin level (not shown). Gripping tool (506) can then be removed, leaving second tube (502b) associated with dismantable retention structure (504), secured in place to the inner wall of the stomach. In some exemplary embodiments, strips (510a,b) are toothed strips configured to move along a screw element in response to application of rotational motion on the screw element, to thereby move the point of association with the tube between inside the stomach and outside the body. For example, strips (510 a,b) may include an integrated gear rack on one side thereof, which is configured to engage and move along a screw element embedded in dismantable retention structure (504). The embedded screw element can be configured to engage with an external screwdriver that can be inserted through the tube's lumen and operated to cause movement of the strips.

Reference is now made to FIGS. 6A-6B, which respectively show schematic illustrations of a perspective view and a longitudinal cross-sectional view of a gripping member (620) and tube (602) according to some embodiments of the present invention.

Gripping member (620) comprises a fitting element (616) comprising two clamp elements (610 a,b), and a plug element (612). Fitting element (616) is a cylindrical hollow element comprising in its lumen a plurality of clamps connected to (or integrally formed with) an internal wall thereof. Clamps (610 a,b) comprise one end attached to (or integrally formed with) the inner wall of fitting element (616), and an opposite end extending into the lumen of fitting element (616). Clamps (610 a,b) are operable to move from a first position in which distal ends thereof extend towards the center of the lumen of fitting element (616), to a second position in which the distal ends thereof are pushed against the inner wall of fitting element (616), and vice versa. Fitting element (616) is configured to engage with a distal end of tube (602) via clamps (610 a,b). When clamps (610 a,b) are in the first position, tube (602) can be inserted/removed. When clamps (610 a,b) are in the second position, tube (602) is firmly gripped.

Plug (612) comprises an outer wall (618) enclosing a lumen and an internal cylinder (614) within the lumen. Plug (612) is hollow and open at both ends. The upper end of plug (612), intended to face the stomach's lumen, is configured for engagement with an external gripping tool, such as a screwdriver. In the illustrated embodiment, the upper open end has a hexagonal-shaped opening. Plug (612) is operable to engage with fitting element (616). When plug (612) is moved at the direction showed by the longitudinal arrows and engaged with fitting element (616), outer wall (618) surrounds fitting element (616) while internal cylinder (614) pushes clamps (610 a,b) against the inner wall of fitting element (616) at the direction showed by the horizontal arrows, such that the distal end of tube (602) is firmly held. Operation of plug (612) can be performed by a gripping tool (not shown). For example, plug (612) may include an internal thread mechanism configured to engage with an external screwdriver inserted through the lumen of tube (602).

In some embodiments, a retention structure can be connected to (or integrally formed with) the plug and/or fitting element. According to these embodiments, the retention structure can be held inside the stomach via plug and fitting element while the tube is replaced. When the tube is no longer needed, the retention structure can be released by the release of the plug/fitting element.

Figure 7C:
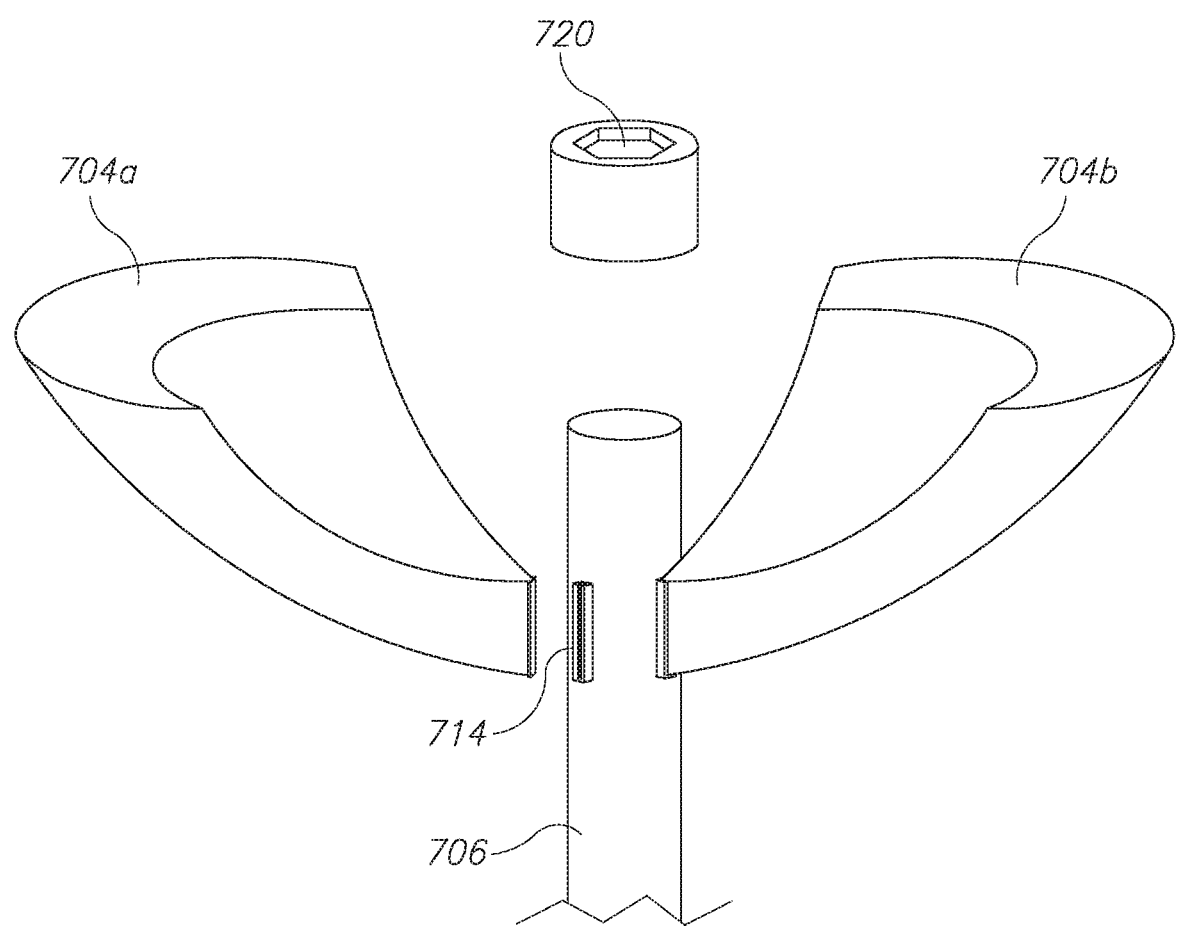
FIG. 7C is a schematic illustration of a side view of a gastrostomy tube and retention structure according to some embodiments of the present invention.

Reference is now made to FIG. 7A-7C, which show schematic illustrations of a gastrostomy tube and retention structure according to some embodiments of the present invention. The retention structure is shown in assembled (FIG. 7A) and disassembled (FIG. 7B) forms. FIG. 7C is a close-up side view of a distal end of the tube.

A retention structure (700) is shown in association with a gastrostomy tube (702) having a first (distal) end (706) configured to be positioned inside the stomach of a patient, and a second (proximal) end (708) configured to extend out of the patient body. The retention structure (700) comprises a plurality of retention elements (704a-d) extending radially outwardly around the first end (706) of the tube, and being reversibly assembled thereto. Each retention element has a proximal end (710) and a distal end (712).

As used herein, a "plurality" refers to two or more, for example, three or more, four or more, five or more, six or more, Each possibility represents a separate embodiment of the invention.

The retention elements may be designed in various forms, including symmetrical and asymmetrical. In some embodiments, retention elements that constitute one retention structure are of the same shape. In other embodiments, they are of different shapes.

Examples of possible shapes of the retention elements include, but are not limited to, rounded or oval, with a tapered end. The retention elements illustrated in FIGS. 7A-7C are of similar size and petal-like shape, having a tapered proximal end and a wider distal end.

Typically, the retention elements are sized to enable smooth passage through the gastrointestinal tract of the patient. They are typically designed to have blunt ends, in order to prevent perforation or other damages to the internal walls of the digestive system of the patient. The total diameter of the retention structure may range from about 1-3 cm, for example about 2-3 cm, about 2-2.5 cm. Each possibility represents separate embodiments of the invention. For adult tubes, the total diameter is typically about 2.5 cm.

In some embodiment, at least one of the retention elements comprises a weight embedded therein. Such weight may prevent floating of the device and/or back up into the esophagus, particularly in infants. Such weight may also be used for imaging purposes, e.g. X-ray imaging.

FIG. 7B-7C show first end (706) of the tube, which comprises a plurality of grooves (714) cut therein. Each groove is configured to accommodate at least one of the plurality of retention elements (704a-d) through a proximal end (710) of said retention elements. In some embodiments, the set of grooves are substantially equidistantly disposed within the end of the tube. The widths and depths of the grooves could vary in both size and shape. In some embodiments, the grooves are cut in the tube. In other embodiments, there is an intermediate layer, or substance, placed around the top of the tube that contains the grooves and integrates the retention elements thereto.

In the illustrated embodiment, retention elements (704a-d) are secured to tube (702) by plug (720) Plug (720) is hollow and open at both ends. Plug (720) is operable to reversibly engage with distal end (706) of tube (702). When in the engaged position, plug (720) prevents retention elements (704a-d) from dismantling from tube (702). When in the disengaged position, retention elements (704a-d) can dismantle from tube (702) and be released into the stomach. The upper end of plug (720), intended to face the stomach's lumen, is configured for engagement with an external gripping tool, such as screwdriver (716). In the illustrated embodiment, the upper open end has a hexagonal-shaped opening.

In some embodiments, the retention elements can be fixed to the grooves through at east one removable pin (not shown). The removable pin(s) is accessible from the lumen of the tube and is configured to be released by a tool, such as a screwdriver inserted through the lumen.

The retention structure of the present invention can be manufactured in any number of different sizes according to the size of the associated tube.

In some embodiments, the retention structure is made from resilient materials. In other embodiments, semi-rigid materials are used. In some embodiments, the retention structure is made from the same flexible non-toxic materials as the gastrostomy tubes such as biocompatible polymers, including silicone rubber, silicone elastomers, polyurethane, silicone copolymers, polypropylene and/or other similar materials or combinations thereof typically used in the art. As noted above, the retention structure may include one or more weights embedded therein.

In some embodiments, the retention elements that constitute the retention structure may be formed of a material that is decomposed in the acidic environment of the stomach. According to these embodiments, it is possible to coat each element with a protective layer that is removed once the elements are released from the gastrostomy tube. Thus, upon their disassembly, the coating is removed from the retention elements and they become exposed to the surrounding acidity, and eventually get degraded.

When used with a gastrostomy feeding tube, the tube typically contains a connecting element at the second, proximal end thereof that extends outside the body for the attachment of a nutrition or medicinal source as is known in the art.

Reference is now made to FIGS. 8A-8B, which show schematic illustrations of another gastrostomy tube and retention structure according to some embodiments of the present invention. The retention structure is shown in partially assembled form.

A retention structure (800) is shown in association with one end (806) of a gastrostomy tube (802), intended to face a lumen of a subject's stomach. Retention structure (800) comprises a plurality of retention elements (804 a, b, c) extending radially outwardly around the one end (806) of the tube, and being removably assembled thereto. Each retention element has a proximal end (810 *a, b, c*) and a distal end (812 *a, b, c*). The retention elements illustrated in FIGS. 8A-8B are of similar size and petal-like shape. Proximal ends (810 *a, b, c*) of the retention elements are generally rounded, with a rounded central bore (814) cut therein, which is configured for threading onto tip (806) of tube (802). The retention elements illustrated in FIGS. 8A-8B are secured and fixed to tip (806) of tube (802) through at least one removable screw-nut (816). The screw-nut is accessible from the lumen of the tube and is configured to be released by a screwdriver (818) inserted through the lumen.

Tube (802) comprises a support base (820) approximate to one end (806), which is configured to mount thereon said plurality of retention elements (804 *a, b, c*). The plurality of retention elements illustrated in FIGS. 8A-8B may be sequentially threaded onto the tip of the tube prior to insertion into a subject, for example, in the case of an endoscopic procedure, or following insertion of the tube, for example, in the case of a surgical procedure. Retention elements (804 *a, b, c*) are configured to be secured in place using removable screw-nut (816). When the PEG tube is no longer needed, the screw-nut can be removed by inserting the screwdriver inside the lumen of the tube, thereby facilitating release of the retention elements and extraction of the tube.

Figure 8C:
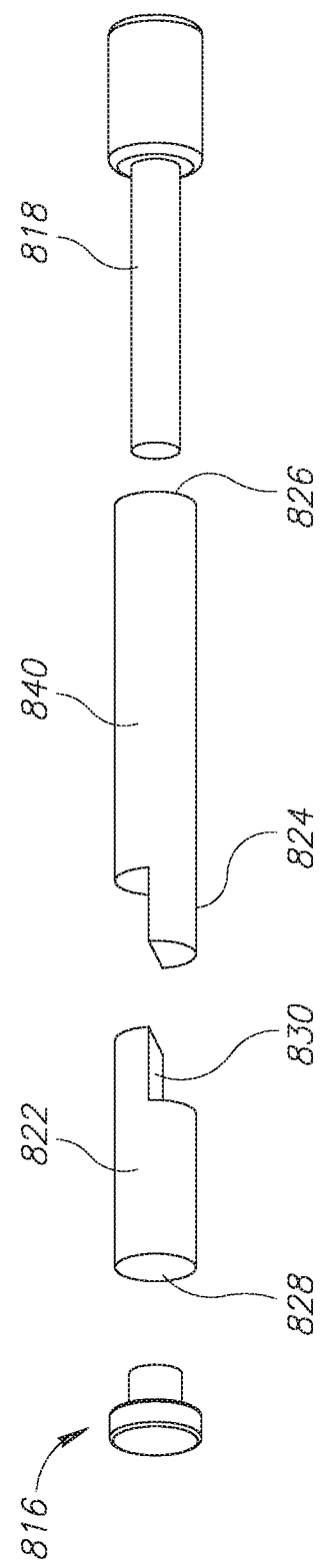
FIG. 8C is a schematic illustration of a fixation element that may be used with a gastrostomy tube according to some embodiments of the present invention.

In some embodiments, a fixation element (840) may be used, as illustrated in FIG. 8C, to prevent rotation of the tip of the tube upon operation of a screwdriver to release the screw-nut and subsequently the retention elements. The fixation element may be a rigid or semi-rigid element inserted through the lumen of the tube, that is configured to fixate the interface point of the screw-nut and tube, thereby preventing movement of the tube. The fixation element may be particularly beneficial when highly resilient tubes are used, where operation of a screwdriver inside the lumen of the tube may result in rotation of the tip of the tube, rather than the screw-nut.

It is to be understood that the fixation element may be used with any of the retention structures and tubes disclosed herein.

Fixation element (840) may be connected to a matching element (822) integrally formed within the tube or connected to the tip of the tube. As illustrated in FIG. 8C, fixation element (840) comprises a first end (824) and a second end (826), the first end is configured to connect to matching element (822), and the second end is configured to allow passage of a tool, such as screwdriver (818), therethrough. Matching element (822) comprises a first end (828) configured to attach to a screw-nut or pin (816), and a second end (830) configured to attach to fixation element (840). It is understood that fixation element (840), matching element (822) and screw-nut (816) are hollow and open at both ends to allow passage of food and/or medications therethrough.

Figure 9A:
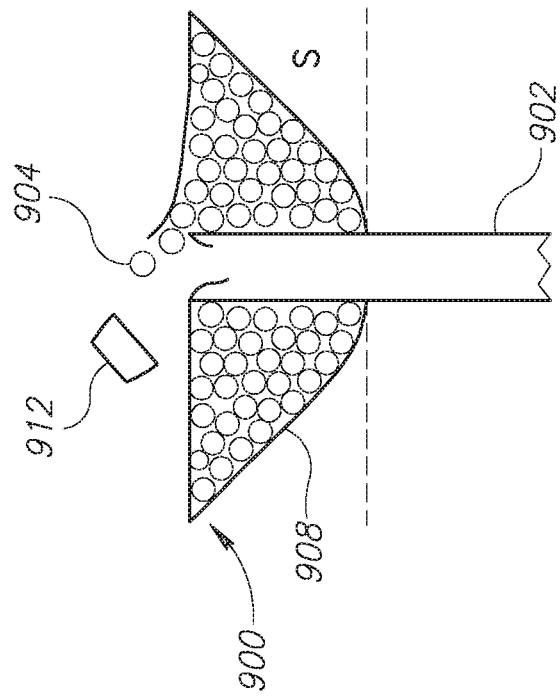
FIGS. 9A-9D are schematic illustrations of side views of a tube and retention structures according to additional embodiments of the present invention.
Figure 9B:
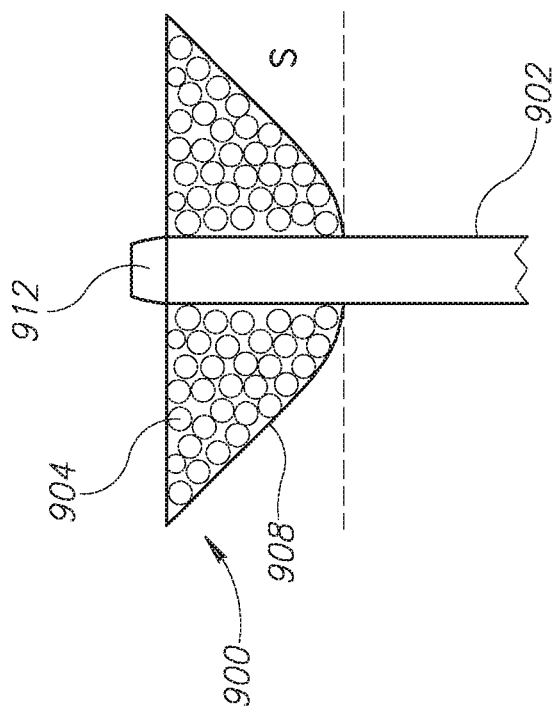

Reference is now made to FIGS. 9A-9B, which show schematic illustrations of a gastrostomy tube and retention structure according to additional embodiments of the present invention. The retention structure is shown in assembled (FIG. 9A) and partially disassembled (FIG. 9B) forms.

A retention structure (900) is shown in association with a gastrostomy tube (902). Retention structure (900) is shown in reference to the stomach wall (dotted line), extending into the stomach (S) of the subject.

Retention structure (900) comprises a plurality of retention elements (904) (spheres) enclosed within an envelope (908). Envelope (908) comprises plug (912) at a distal end thereof. Plug (912) is hollow and open at both ends. Plug (912) is accessible from the lumen of tube (902) and is configured to be released by a tool inserted through the lumen. As illustrated in FIG. 9B, removal of plug (912) facilitates opening of said envelope and release of the plurality of retention elements into the subject's stomach.

Figure 9D:
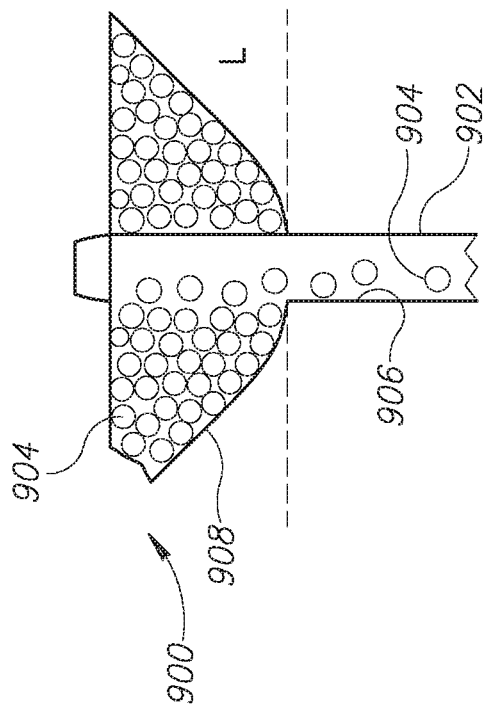
Figure 9C:
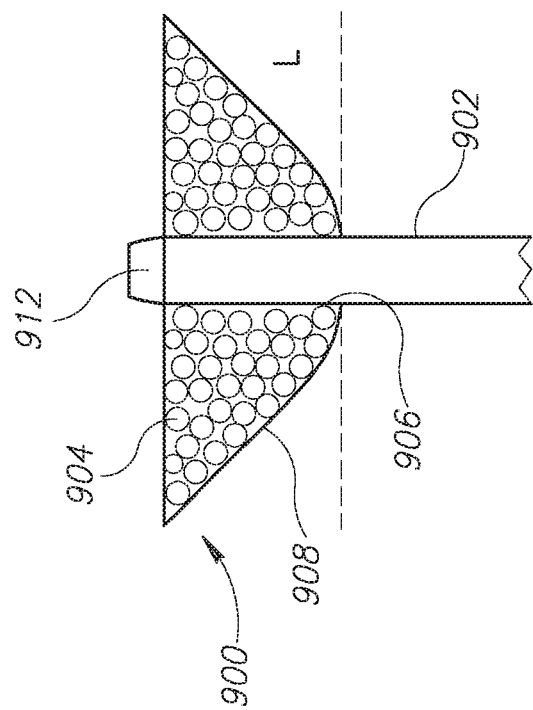

Reference is now made to FIGS. 9C-9D, which show schematic illustrations of an ostomy tube and retention structure suitable for ostomy procedures performed in closed cavities according to some embodiments of the present invention. The retention structure is shown in assembled (FIG. 9C) and partially disassembled (FIG. 9D) forms.

A retention structure (900) is shown in association with a tube (902). Retention structure (900) is shown in reference to the wall of the body lumen (dotted line), extending into body lumen (L) of the patient.

Retention structure (900) comprises a plurality of retention elements (904) (spheres) enclosed within an envelope (908). Retention structure (900) comprises at least one wall (906) separating the inner lumen of said envelope (908) from the inner lumen of said tube (902). Wall (906) is accessible from the lumen of tube (902) and is configured to be released by a tool inserted through the lumen.

As illustrated in FIG. 9D, upon removal of wall (906), retention elements (904) contained within envelope (908) are released into the lumen of the tube and may be collected outside the body of the patient.

Figure 10:
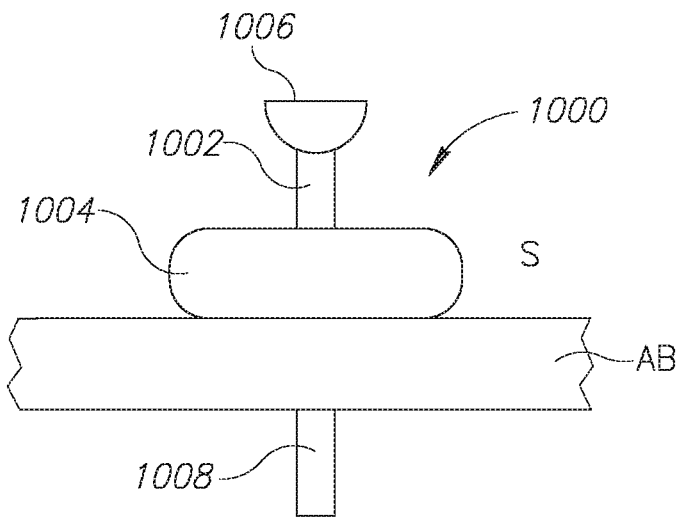
FIG. 10 is a schematic illustration of a side view of a tube and retention structure according to additional embodiments of the present invention.

Reference is now made to FIG. 10, which shows a schematic illustration of a gastrostomy tube and retention structure according to additional embodiments of the present invention.

A retention structure (1000) is shown in association with a gastrostomy tube (1002). Retention structure (1000) is shown in reference to the abdominal wall (AB). extending into the stomach (S) of the patient. Retention structure (1000) comprises a dismantlable retention element (1004) comprising a bore for the passage of tube (1002) therein. The bore is not visible in the side view. Retention structure (1000) further comprises a non-dismantable resilient retention element (1006) affixed to (or integrally formed with) a distal end of tube (1002), extending into the lumen of the stomach. Upon pulling of tube (1002) via its external portion (1008), non-dismantlable element (1006) can fold and allow the retraction and removal of the tube, Dismantlable element (1004) can then be released into the stomach and be expelled naturally.

Reference is now made to FIGS. 11A-11F, which show a schematic illustration of a tubing system according to some embodiments of the present invention, and a method of tube placement, replacement and removal utilizing such system. The illustrated tubing system is suitable for various ostomy procedures and drain tubes, including for example urinary, chest and abdominal tubes.

Figures 11A, 11B:
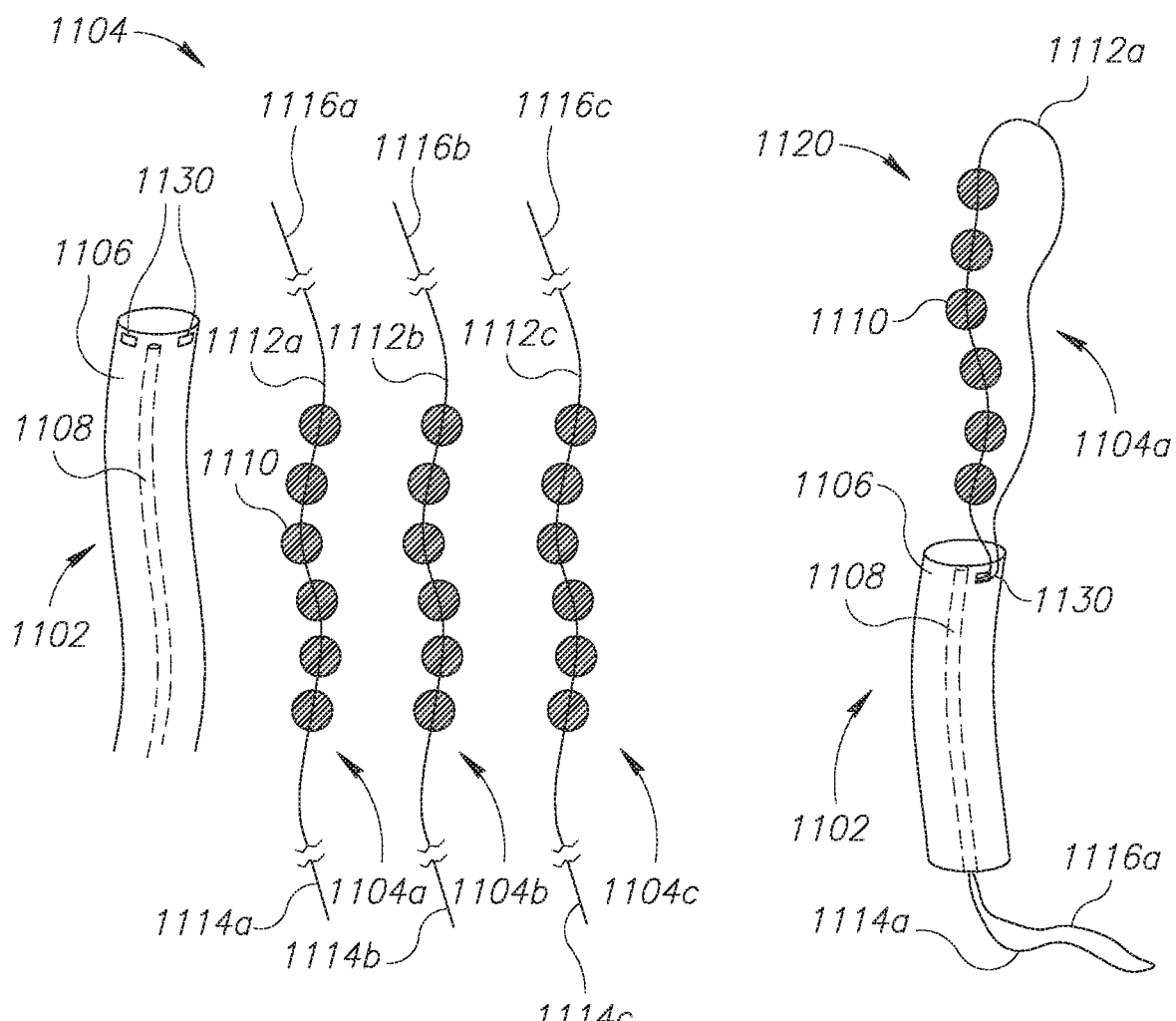
FIGS. 11A-11F show a schematic illustration of a tubing system and a method of tube placement, replacement and removal according to some embodiments of the present invention.

FIG. 11A schematically shows tube (1102) and dismantlable retention structure (1104), which is composed of a plurality of retention elements (1104 *a,b,c*), each composed of a set of beads (1110). Each set of beads (1110) is threaded on, or integrally formed with, a gripping member in the form of an elongated flexible cable (1112 *a, b, c*). Each cable (1112 *a, b, c*) comprises a proximal end (1114 *a, b, c*) and a distal end (1116 *a, b, c*). Each cable is further configured for association with tube (1102).

Tube (1102) comprises an outer wall (1106) enclosing a lumen, and an internal channel (1108) within the lumen. The lumen surrounding internal channel (1108) is configured for the passage of food, medications and the like. Internal channel (1108) is configured for receiving one or more cables, Outer wall (1106) comprises a plurality of apertures (1130) cut therein, at a vicinity of a distal end of tube (1102), that is configured to be positioned inside a body lumen of a subject. Each aperture is configured to enable threading one or more cables therethrough. Typically, the number of apertures corresponds to the number of cables to be used with the tube.

FIG. 11B shows association of tube (1102) with cable (1112a) and its set of beads (1110) that constitute retention element (1104a), which is typically performed prior to insertion into a subject. Cable (1112a) is folded to form a loop such that proximal end (1114a) and distal end (1116a) of cable (1112a) can be inserted through an aperture (1130) in outer wall (1106) of tube (1102), and further into internal lumen (1108) of tube (1102).

Figure 11C:
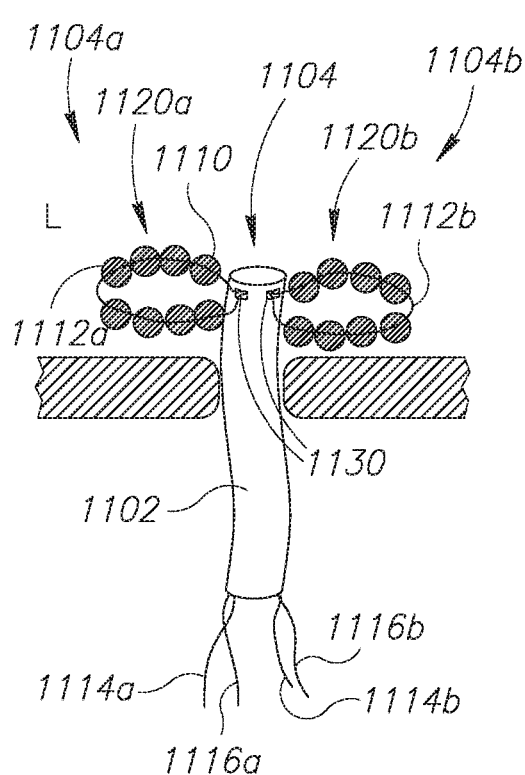

The size of each aperture (1130) is sufficiently large to enable insertion of the two ends of the folded cable, yet sufficiently small such that beads (1110) cannot pass therethrough. Cable (1112a) is positioned inside tube (1102) such that the portion of cable. (1112a) that contains the set of beads (1110) forms a loop (1120) that remains outside a distal end of tube (1102), that is configured to face a body lumen. The two ends of cable (1112a) extend outside a proximal end of tube (1102), intended to face outside the body. Loop (1120) is operable to bend to assume a petal-like configuration extending radially outwardly from a distal end of tube (1102), as shown in FIG. 11C. Similar to the insertion and positioning of retention element (1104a) inside tube (1102), additional retention elements (1104 b, c) can be similarly operated, resulting in a petal-like structure extending radially outwardy around a distal end of tube.

FIG. 11C shows a schematic illustration of tube (1102) and dismantlable retention structure (1104) following insertion and positioning inside a body lumen (L) of a subject. The point of association of the gripping member (cables 1112 a, b) with dismantlable retention structure (sets of beads) and tube is located inside the body lumen.

In the illustrated embodiment, dismantlable retention structure (1104) comprises two retention elements (two sets of beads 1104 a,b). In other embodiments, additional retention elements may be used, for example three, four, five, or six retention elements. Each of retention elements (1104 a,b) comprises a set of beads (1110) threaded on, or integrally formed, with a cable (1112 a, b). Each cable is folded such that proximal ends (1114 a,b) and distal ends (1116 a,b) of the cables extend outside a proximal end of tube (1102), outside the body. The portion of each cable that contains beads (1110) forms a loop (1120 a,b), that is canted over relative to the distal end of tube (1102), towards the inner wall of the body lumen, for example, positioned substantially perpendicular to the distal end of tube (1102). Loops (1120 a,b) collectively form a petal-like structure extending radially outwardly around the distal end of tube (1102) and secure the tube in place.

Figure 11D:
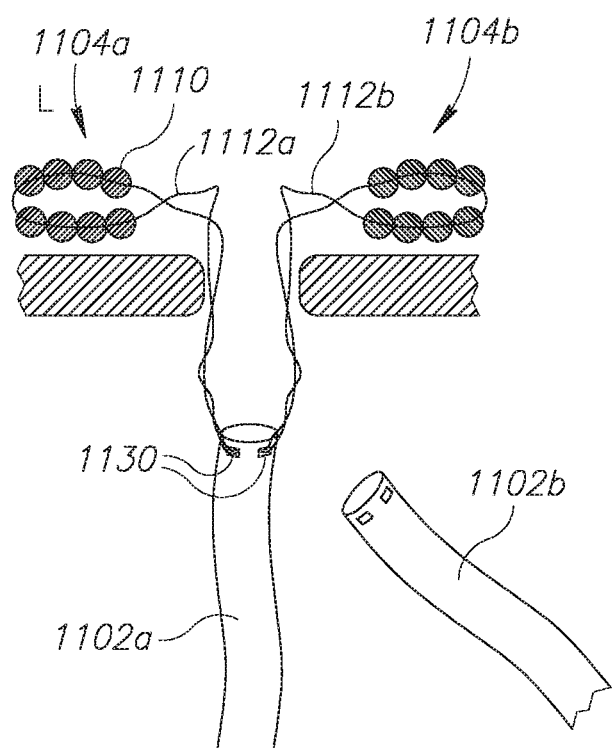

FIG. 11D schematically illustrates tube replacement in the tubing system described in FIGS. 11A-11C. In order to replace first tube (1102a), first tube (1102a) is operated to disengage and retract from cables (1112 a,b). Cables (1112 a,b) are held in place while first tube (1102a) is removed (for example, the portion of cables (1112 a, b) that protrudes outside the body can be held by a clinical practitioner), and second tube (1102b) is placed over cables (1112 a,b) and secured to retention elements (1104 a,b).

Figure 11E:
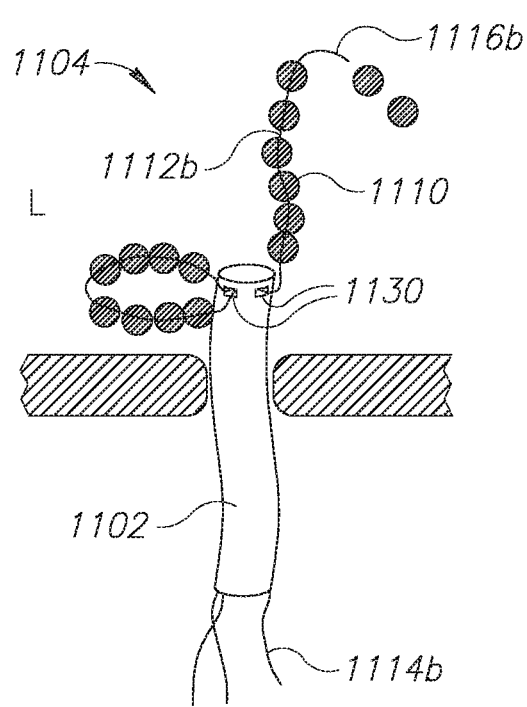

FIG. 11E schematically illustrates removal of tube (1102) and release of retention structure (1104) in case a tube is no longer needed. The illustrated embodiment is suitable for tubes for use in the stomach or other parts of the gastrointestinal tract. A distal end (1116b) of cable (1112b) is operated to move through tube (1102) until it disengages from the tube and protrudes outside the distal end of tube (1102), inside the body lumen (for example, inside the stomach). In the illustrated embodiment, beads (1110) are threaded on cable (1112b) and operable to be released from cable (1112b) into the stomach lumen, and be expelled naturally. Cable (1112b) is then retracted through tube (1102) in the opposite direction, outside the body. Cable (1112a) and its beads can be similarly released and removed. Tube (1102) can then be retracted and removed as well.

Figure 11F:
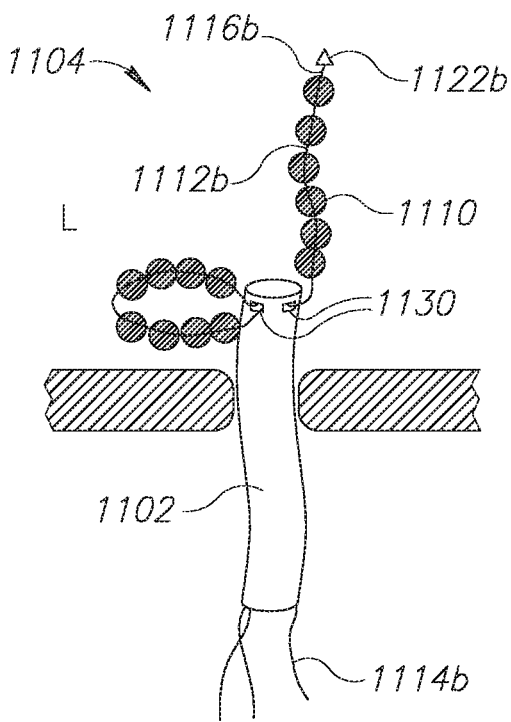

FIG. 11F schematically illustrates removal of tube (1102) and release of retention structure (1104) in case a tube is no longer needed. The illustrated embodiment is suitable for tubes for use in the stomach or other parts of the gastrointestinal tract, as well as for tubes to be placed in closed body cavities.

A distal end (1116b) of cable (1112b) is operated to move through tube (1102) until it disengages from the tube and protrudes outside the distal end of tube (1102), into the body lumen. In the illustrated embodiment, beads (1110) are threaded on cable (1112b). A stop element (1122b) adjacent to, or at, distal end (1116b) of cable (1112b) prevents beads (1110) from being released into the body lumen. Similarly, a distal end (1116a) of cable (1112a) can be operated to move through tube (1102) until it disengages from the tube and protrudes outside the distal end of tube (1102), into the body lumen. When the distal ends of all cables are disengaged from the tube and protrude into the body lumen, tube (1102) can be retracted outside the body. Cables (1112 a, b) can then be retracted sequentially outside the body as well.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A gastrostomy tubing system comprising:
   a gastrostomy tube comprising a distal side and a proximal side, the distal side is configured to be positioned in a stomach of a subject's body and the proximal side is configured to extend outside the subject's body; and
   a dismantlable retention structure constructed from at least three retention pieces, removably assembled to said distal side of said gastrostomy tube, wherein each of said at least three retention pieces extend radially outwards from said gastrostomy tube to allow contact with an inner wall of the stomach;
   wherein, when the dismantlable retention structure is inside the stomach and said at least three retention pieces contact the inner wall of the stomach, the at least three retention pieces are configured to secure the gastrostomy tube to the inner wall of the stomach such that the gastrostomy tube is secured against removal from said stomach; and,
   wherein said dismantlable retention structure comprises a securing portion accessible to an engagement tool from an inner lumen of said gastrostomy tube and comprises a geometry that matches a geometry of said engagement tool, wherein said securing portion is configured to secure said dismantlable retention structure to said gastrostomy tube;

wherein dismantling of the dismantlable retention structure from said gastrostomy tube is configured to occur when a distal end of said engagement tool is extended into the subject's body through said inner lumen of said gastrostomy tube such that said engagement tool contacts said securing portion of the dismantlable retention structure from said inner lumen of said gastrostomy tube thereby disassembling the dismantlable retention structure into said at least three retention pieces.

2. The gastrostomy tubing system of claim 1, wherein said at least three retention pieces of said dismantlable retention structure are configured to assemble to the distal side of said gastrostomy tube by one or more retractable cables.

3. The gastrostomy tubing system of claim 1, wherein said at least three retention pieces are configured to directly attach to said gastrostomy tube.

4. The gastrostomy tubing system of claim 1, wherein said securing portion comprises a hollow plug, wherein said hollow plug is configured to hold said at least three retention pieces onto said gastrostomy tube.

5. The gastrostomy tubing system of claim 4, wherein said hollow plug is sized and shaped to engage with said distal end of said engagement tool.

6. The gastrostomy tubing system of claim 5, wherein said hollow plug is configured to be released from said gastrostomy tube by rotation of said engagement tool in contact with said hollow plug, thereby dismantling said dismantlable retention structure from said gastrostomy tube.

7. The gastrostomy tubing system of claim 4, wherein said hollow plug includes a thread which, upon application of rotational motion, is configured to disassemble said at least three retention pieces.

8. The gastrostomy tubing system of claim 4, wherein said hollow plug is open at both ends.

9. The gastrostomy tubing system of claim 8, wherein one of the open ends is hexagonal-shaped.

10. The gastrostomy tubing system of claim 1, wherein said securing portion comprises one or more removable screw-nuts, and wherein said at least three retention pieces are configured to assemble to the distal side of said gastrostomy tube by said one or more removable screw-nuts.

11. The gastrostomy tubing system of claim 1, wherein each of said at least three retention pieces contact said securing portion and have a petal-like shape with a tapered proximal end and a wider distal end, wherein each proximal end of each of said at least three retention pieces is configured to be located radially inwardly relative to a corresponding distal end of each of said at least three retention pieces.

12. The gastrostomy tubing system of claim 1, wherein said at least three retention pieces have blunt ends.

13. The gastrostomy tubing system of claim 1, wherein a total diameter of said dismantlable retention structure is 1-3 cm.

14. The gastrostomy tubing system of claim 1, wherein a total diameter of said dismantlable retention structure is about 2.5 cm.

15. The gastrostomy tubing system of claim 1, wherein said dismantlable retention structure comprises silicone rubber.

16. The gastrostomy tubing system of claim 1, comprising a fixation element insertable through said inner lumen and configured to prevent rotation of the gastrostomy tube upon operation of said engagement tool.

17. The gastrostomy tubing system of claim 1, comprising an external bolster, configured to be mounted at a skin surface of said subject, thereby securing said gastrostomy tube in place.

18. The gastrostomy tubing system of claim 1, wherein said at least three retention pieces extend radially away from said gastrostomy tube and define a contact surface with said inner wall of said stomach facing a proximal direction.

19. The gastrostomy tubing system of claim 1, wherein each of said at least three retention pieces is separately connected to said distal side of said gastrostomy tube.

20. The gastrostomy tubing system of claim 1, wherein said at least three retention pieces are separate retention pieces, and wherein said securing portion is configured to release said at least three retention pieces from said gastrostomy tube when contacted by said engagement tool.

21. A kit for gastrostomy comprising:
(i) a gastrostomy tubing system comprising:
a gastrostomy tube comprising a distal side and a proximal side, the distal side is configured to be positioned in a stomach of a subject's body and the proximal side is configured to extend outside the subject's body;
a dismantlable retention structure constructed from at least three retention pieces removably assembled to said distal side of said gastrostomy tube, wherein each of said at least three retention pieces extend radially outward from said gastrostomy tube to allow contact with an inner wall of the stomach;
wherein when the dismantlable retention structure is inside the stomach and said at least three retention pieces contact the inner wall of the stomach, the at least three retention pieces are configured to secure the gastrostomy tube to the inner wall of the stomach such that the gastrostomy tube is secured against removal from the stomach and,
wherein said dismantlable retention structure comprising a securing portion accessible to an engagement tool from an inner lumen of said gastrostomy tube and comprises a geometry that matches a geometry of said engagement tool, wherein said securing portion is configured to secure said dismantable retention structure to said gastrostomy tube;
wherein the dismantlable retention structure is configured to dismantle from said gastrostomy tube into the at least three retention pieces and facilitate removal of the gastrostomy tube;
(ii) an engagement tool configured for insertion through said inner lumen of said gastrostomy tube, a distal portion of said engagement tool configured to engage with the securing portion of said dismantlable retention structure inside the patient's body, wherein dismantling of the dismantlable retention structure into said at least three pieces is configured to occur when a distal end of said engagement tool is extended through said inner lumen of said gastrostomy tube into said subject's body, the engagement tool is configured to be manipulated externally from outside the subject's body such that the distal end contacts the securing portion thereby disassembling the dismantlable retention structure into said at least three retention pieces.

22. The kit for gastrostomy of claim 21, comprising an external bolster, configured to be mounted at a skin surface of said subject, thereby securing said gastrostomy tube in place.

23. The kit of claim 21, wherein each of said at least three retention pieces is separately connected to said distal side of said gastrostomy tube.

24. A gastrostomy tubing system comprising:
a gastrostomy tube comprising a distal side and a proximal side, the distal side is configured to be positioned in a stomach of a subject's body and the proximal side is configured to extend outside the subject's body; and
a dismantlable retention structure constructed from at least three separate retention pieces and a hollow plug, wherein each of the at least three separate retention pieces is assembled to said distal side of said gastrostomy tube, and extending radially outwards from said gastrostomy tube to allow contact with an inner wall of the stomach, wherein said at least three separate retention pieces are secured to said gastrostomy tube by said hollow plug;
wherein, when the dismantlable retention structure is inside the stomach and said at least three separate retention pieces contact the inner wall of the stomach, the at least three separate retention pieces are configured to secure the gastrostomy tube to the inner wall of the stomach such that the gastrostomy tube is secured against removal from said stomach; and,
wherein said hollow plug is contactable by an engagement tool from a lumen of said gastrostomy tube, and comprises a geometry that matches a geometry of said engagement tool;
wherein dismantling of the dismantlable retention structure is configured to occur when a distal end of said engagement tool is extended into the subject's body through said lumen of said gastrostomy tube such that said engagement tool contacts said hollow plug of the dismantlable retention structure thereby disassembling the dismantlable retention structure into said at least three separate retention pieces.

* * * * *